United States Patent
Davis et al.

(10) Patent No.: US 6,180,104 B1
(45) Date of Patent: *Jan. 30, 2001

(54) T CELL RECEPTOR BETA SUBUNIT

(75) Inventors: Mark M. Davis, Mountain View; Stephen M. Hedrick, Solana Beach, both of CA (US)

(73) Assignee: The Board of Trustees of the Leland Stanford Junior University, Stanford, CA (US)

( * ) Notice: Under 35 U.S.C. 154(b), the term of this patent shall be extended for 0 days.

This patent is subject to a terminal disclaimer.

(21) Appl. No.: 09/082,593

(22) Filed: May 20, 1998

Related U.S. Application Data

(62) Division of application No. 08/235,601, filed on Apr. 29, 1994, now Pat. No. 5,840,304, which is a division of application No. 07/924,395, filed on Aug. 3, 1992, now Pat. No. 5,316,925, which is a continuation of application No. 06/663,809, filed on Oct. 22, 1984, now abandoned, which is a continuation-in-part of application No. 06/585,333, filed on Mar. 1, 1984, now abandoned.

(51) Int. Cl.$^7$ .................................................. A61K 39/00
(52) U.S. Cl. .................................. 424/192.1; 424/193.1; 514/2; 530/300; 530/323; 530/350; 530/402
(58) Field of Search ................................. 530/323, 300, 530/350, 402; 514/2; 424/192.1, 193.1

(56) References Cited

U.S. PATENT DOCUMENTS

| | | | |
|---|---|---|---|
| 4,356,270 | 10/1982 | Itakura | 435/317 |
| 4,394,443 | 7/1983 | Weissman et al. | 435/6 |
| 4,446,235 | 5/1984 | Seeburg | 435/91.1 |
| 4,468,464 | 8/1984 | Cohen et al. | 435/317 |
| 4,550,086 | 10/1985 | Reinherz et al. | 436/506 |
| 4,713,332 | 12/1987 | Mak | 435/70.1 |
| 4,874,845 | 10/1989 | Saito et al. | 530/395 |
| 4,923,799 | 5/1990 | Mak | 435/6 |
| 5,316,925 | 5/1994 | Davis et al. | 435/91.2 |
| B1 4,363,877 | 12/1998 | Goodman et al. | 435/320.1 |

FOREIGN PATENT DOCUMENTS

| | | | |
|---|---|---|---|
| 0 180 878 A2 | 5/1986 | (EP) | C12N/15/00 |

OTHER PUBLICATIONS

Acuto, O. et al., "The Human T Cell Receptor: Appearance in Ontogeny and Biochemical Relationship of α and β Subunits on IL-2 Dependent Clones and T Cell Tumors," *Cell*, 34:717–726 (1983).

Acuto, O. et al., "Peptide Variability Exists Within α and β Subunits of the T Cell Receptor for Antigen," *J. Exp. Med.*, 158(4):1368–1373 (1983).

Acuto, O. et al., "Purification and NH$_2$–Terminal Acid Sequencing of the β Subunit of a Human T–Cell Antigen Receptor," *Proc. Natl. Acad. Sci. Usa*, 81(12):3851–3855 (1984).

Allison, J. P. et al., "Tumor–Specific Antigen of Murine T–Lymphoma Defined with Monoclonal Antibody," *J. Immun.*, 129(5):2293–2300 (1982).

Auffray, C. et al., "cDNA Clone for the Heavy Chain of the Human B Cell Alloantigen DC1: Strong Sequence Homology to the HLA–DR Heavy Chain," *Proc. Natl. Acad. Sci. USA*, 79(20):6337–6341 (1982).

Augustin, A. A. et al., "Expression of Idiotype–Like Determinants on Hapten–Specific, MHC–Restricted T Helper Cells, Enriched *in Vitro*," *Regulatory T. Lymphocytes*, Pernis, B. et al., eds., Academic Press, NY, 171–184 (1980).

Berzofsky, J., "T–Cell Activation by Antigen: Promising Clues to Reception Genes and Molecules," *Immun. Today*, 4:299–301 (1983).

Binz, H. et al., "Shared Idiotypic Determinants on B and T Lymphocytes Reactive Against the Same Antigenic Determinants," *J. Exp. Med.*, 142(1):197–211 (1975).

Binz, H. et al., "T Cell Receptors with Allo–Major Histocompatibility Complex Specificity from Rat and Mouse," *J. Exp. Med.*, 154(5):1261–1278 (1981).

Boned, A. et al., "Electromicroelution and Microfingerprinting of Radiolabeled Immunoglobulins from Sodium Dodecyl Sulfate–Polyacrylamide Gels," *J. Immunol. Meth.*, 55(1):99–105 (1982).

Creighton, T. E., "Evolutionary and Genetic Origins of Protein Sequences," *Proteins: Structures and Molecular Principles*, W. H. Freeman & Co., NY, 93–131 (1983).

Bigler, R. D. et al., "Idiotype–Like Molecules on Cells of a Human T Cell Leukemia," *J. Exp. Med.*, 58(3):1000–1005 (1983).

Davis, M. M. et al., "The Isolation of B and T Cell–Specific Genes," *B and T Cell Tumors*, UCLA Symposia on Molecular and Cellular Biology, Vitteta, E. S. et al., eds., Academic Press, NY, 24:215–220 (1982).

Eichmann, K. et al., "Induction of T and B Cell Immunity by Anti–Idiotypic Antibody," *Eur. J. Immunol.*, 5(10):661–666 (1975).

Eshhar, Z. et al., "T–Cell Hybridoma Bearing Heavy Chain Variable Region Determinants Producing (T,G)–A—L–Specific Helper Factor," *Nature*, 286(5770):270–272 (1980).

(List continued on next page.)

*Primary Examiner*—Patrick Nolan
(74) *Attorney, Agent, or Firm*—Daniel M. Becker; Hope Liebke; Fish & Neave

(57) ABSTRACT

Oligonucleotide sequences are provided coding for T-cell-specific antigen receptors or fragments thereof. The oligonucleotide sequences can be used as probes for detecting helper and cytotoxic T-cells, preparing and isolating DNA sequences encoding for the receptor polypeptide, and in constructions for expression of receptor polypeptides or fragments thereof. In addition, processing signals from the receptor subunits can be employed in conjunction with modified wild type oligonucleotide sequences or non-wild type oligonucleotide sequences.

6 Claims, 5 Drawing Sheets

OTHER PUBLICATIONS

Gascoigne, N. R. J. et al., "Genomic Organization and Sequence of T–Cell Receptor β–Chain Constant–and Joining–Region Genes," *Nature*, 310(5976):387–391 (1984).

Golub, E. S. et al., *Immunology, A Synthesis*, 2nd Edition, Sinauer Associates, Inc., Sunderland, MA, (1991).

Hamilton, D. P., "Publishing by —and for?—the Numbers," *Science*, 250:1331–1332 (1990).

Harlow, E. et al., eds., "Comments: Troubleshooting—Bad Backgrounds," *Antibodies, A Laboratory Manual*, Cold Spring Harbor Laboratory, chap. 11:469–470 (1988).

Haskins, K. et al., "The Major Histocompatibility Complex–Restricted Antigen Receptor on T Cells," *J. Exp. Med.*, 157(4):1149–1169 (1983).

Heber–Katz, E. et al., "Contribution of Antigen–Presenting Cell Major Histocompatibility Complex Gene Products to the Specificity of Antigen–Induced T Cell Activation," *J. Exp. Med.*, 155(4):1086–1099 (1982).

Hedrick, S. M. et al., "Isolation of cDNA Colnes Encodong T Cell–Specific Membrane–Associated Proteins," *Nature*, 308(5955):149–153 (1984).

Hedrick, S. M. et al., "The Fine Specificity of Antigen and Ia Determinant Recognition by T Cell Hybridoma Clones Specific for Pigeon Cytochrome c," *Cell*, 30:141–152 (1982).

Hercend, T. et al., "Identification of a Clonally Restricted 90kD Heterodimer on Two Human Cloned Natural Killer Cell Lines," *J. Exp. Med.*, 158(5):1547–1560 (1983).

Kappler, J. et al., "The Mouse T Cell Receptor: Comparison of MHC–Restricted Receptors on Two T Cell Hybridomas," *Cell*, 34:727–737 (1983).

Kappler, J. et al., "The Major Histocompatibility Complex–restricted Antigen Receptor on T Cells in Mouse and Man: Identification of Constant and Variable Peptides," *Cell*, 35:295–302 (1983).

Kavaler, J. et al., "Localization of a T–Cell Receptor Diversity–Region Element," *Nature*, 310(5976):421–423 (1984).

Kim, K. J. et al., "Establishment and Characterization of BALB/c Lymphoma Lines with B Cell Properties," *J. Immunol.*, 122(2):549–554 (1979).

Kim, K. J. et al., "Characteristics of BALB/C T Cell Lymphomas Grown as Continuous *in Vitro* Lines," *J. Immunol.*, 121(1):339–344 (1978).

Kronenberg, M. et al., "Helper and Killer T Cells Do Not Express B Cell Immunoglobulin Joining and Constant Region Gene Segments," *J. Exp. Med.*, 152(6):1745–1761 (1980).

Kronenberg, M. et al., "Three T Cell Hybridomas Do Not Contain Detectable Heavy Chain Variable Gene Transcripts," *J. Exp. Med.*, 158(1):210–227 (1983).

Kronenberg, M. et al., "Finding the T–Cell Antigen Receptor: Past Attempts and Future Promise," *Cell*, 34(2):327–329 (1983).

Kyte, J. et al., "A Simple Method for Displaying the Hydropathic Character of a Protein," *J. Mol. Biol.*, 157:105–132 (1982).

Lewin, R., "When Does Homology Mean Something Else?," *Science*, 237:1570 (1987).

Marrack, P. et al., "Antigen–Specific, Major Histocompatibility Complex–Restricted T Cell Receptors," *Immun. Rev.*, 76:131–145 (1983).

Marrack, P. et al., "The Major Histocompatibility Complex–Restricted Antigen Receptor on T Cells," *J. Exp. Med.*, 158(5):1635–1646 (1983).

Marx, J. L., "Likely T Cell Receptor Gene Cloned," *Science*, 221(4617):1278–1279 (1983).

Marx, J. L., "The T Cell Receptor —At Hand at Last," *Science*, 221(4609):444–446 (1983).

Maxam, A. M. et al., "A New Method for Sequencing DNA," *Proc. Natl. Acad. Sci. USA*, 74(2):560–564 (1977).

Maxam, A. M. et al., "Sequencing End–Labeled DNA with Base–Specific Chemical Cleavages," *Methods in Enzymology*, Grossman, L. et al., eds., Academic Press, 65:499–560 (1980).

McIntyre, B. W. et al., "The Mouse T Cell Receptor: Structural Heterogeneity of Molecules of Normal T Cells Defined by Xenoantiserum," *Cell*, 34:739–746 (1983).

Meuer, S. C. et al., "Antigen–Like Effects of Monoclonal Antibodies Directed at Receptors on Human T Cell Clones," *J. Exp. Med.*, 158(3):988–993 (1983).

Meuer, S. C. et al., "Clonotypic Structures Involved in Antigen–Specific Human T Cell Function," *J. Exp. Med.*, 157(2):705–719 (1983).

Meuer, S. C. et al., "Evidence for the T3–Associated 90K Heterodimer as the T–Cell Antigen Receptor," *Nature*, 303(5920):808–810 (1983).

Meuer, S. C. et al., "Identification of the Receptor for Antigen and Major Histocompatibility Complex on Human Inducer T Lymphocytes," *Science*, 222:1239–1241 (1983).

Mushinski, J. F. et al., "Mouse Immunoglobulin D: Construction and Characterization of a Cloned δ Chain cDNA," *Proc. Natl. Acad. Sci. USA*, 77(12):7405–7409 (1980).

Reinherz, E. L. et al., "Comparison of T3–Associated 49–and 43–Kilodalton Cell Surace Molecules on Individual Human T–Cell Clones: Evidence for Peptide Variability in T–Cell Receptor Structures," *Proc. Natl. Acad. Sci. USA*, 80(13):4104–4108 (1983).

Saito, H. et al., "Complete Primary Structure of a Heterodimeric T–Cell Receptor Deduced from cDNA Sequences," *Nature*, 309:757–762 (1984).

Samelson, L. E. et al., "T Cell Clone–Specific Alloantisera that Inhibit or Stimulate Antigen–Induced T Cell Activation," *J. Immun.*, 131(6):2645–2650 (1983).

Samelson, L. E. et al., "Monoclonal Antibodies Against the Antigen Receptor on a Cloned T–Cell Hybrid," *Proc. Natl. Acad. Sci. USA*, 80(22):6972–6976 (1983).

Sargent, T. D. et al., "Differential Gene Expression in the Gastrula of *Xenopus laevis*," *Science*, 222(4620):135–139 (1983).

Siu, G. et al., "The Human T Cell Antigen Receptor is Encoded by Variable, Diversity, and Joining Gene Segments That Rearrange to Generate a Complete V Gene," *Cell*, 37:393–401 (1984).

Springer, T. A., "Immunoprecipitation," *Current Protocols in Immunology*, J. E. Coligan et al., eds., Greene Publishing Associates and Wiley–Interscience, NY, Unit 8.3:8.3.1–8.3.10 (1991).

Tonegawa, S., "Somatic Generation of Antibody Diversity," *Nature*, 302(5909):575–5810 (1983).

Vieira, J. et al., "The pUC Plasmids, an M13mp7–Derived System for Insertion Mutagenesis and Sequencing with Synthetic Universal Primers," *Gene*, 19(3):259–268 (1982).

Waldmann, T. A. et al., "Rearrangements of Genes for the Antigen Receptro on T Cells as Markers of Lineage and Clonality in Human Lymphoid Neoplasms," *N. Eng. J. Med.*, 313(13):776–783 (1985).

Webb, D. R. et al., "Antigen–Specific Factors: An Overview," *Methods in Enzymology*, DiSabato, G. et al., eds., Academic Press, NY, 116:295–303 (1985).

White, J. et al., "Use of I Region–Restricted, Antigen–Specific T Cell Hybridomas to Produce Idiotypically Specific Anti–Receptor Antibodies," *J. Immun.*, 130(3):1033–1037 (1983).

Wilbur, W. J. et al., "Rapid Similarity Searches of Nucleic Acid and Protein Data Banks," *Proc. Natl. Acad. Sci. USA*, 80(3):726–730 (1983).

Williams, A. F. "The T–Lymphocyte Antigen Receptor—Elusive No More," *Nature*, 308(5955):108–109 (1984).

Yanagi, Y. et al., "A Human T Cell–Specific cDNA Clone Encodes a Protein Having Extensive Homology to Immunoglobulin Chains," *Nature*, 308:145–148 (1984).

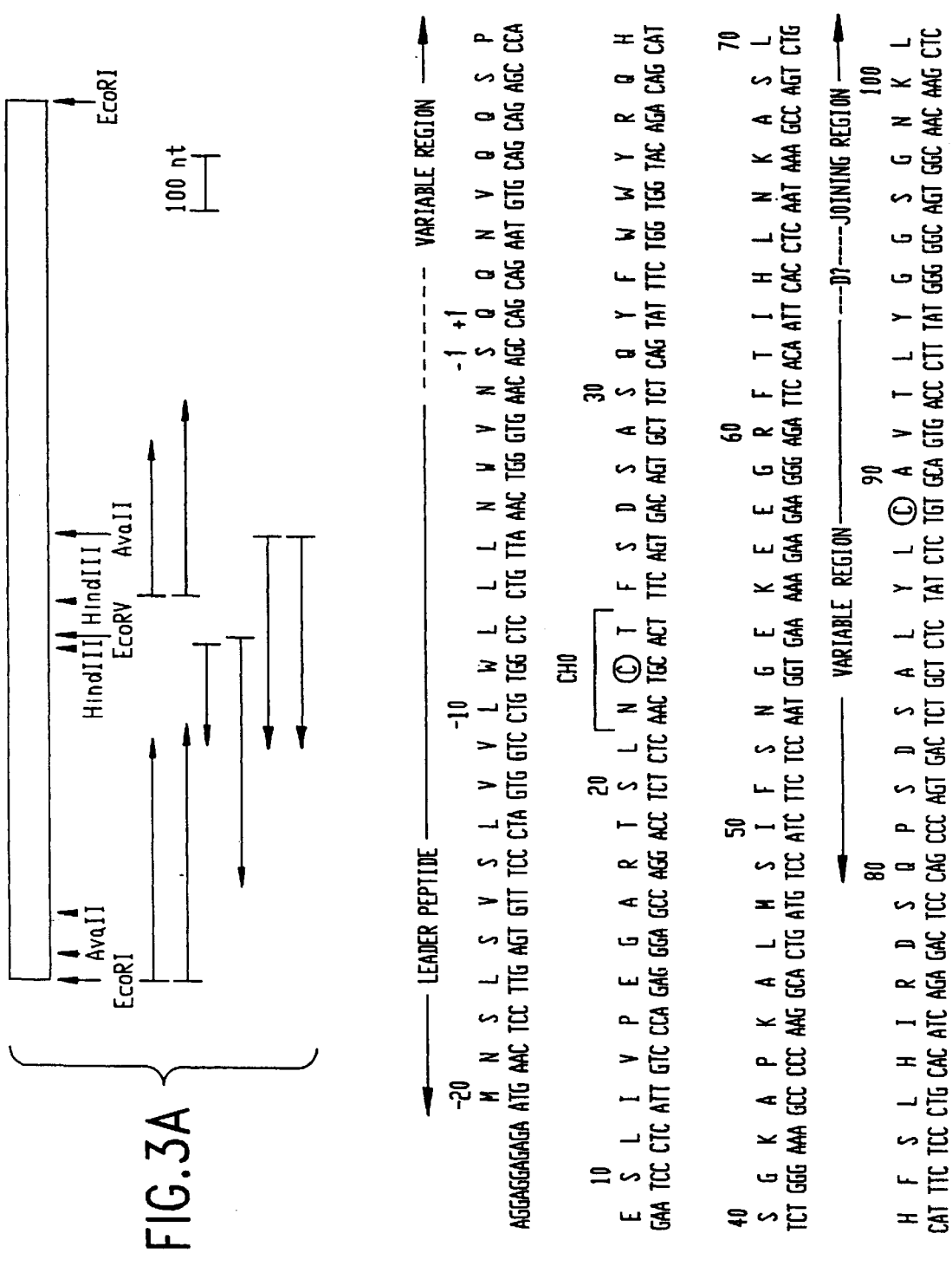

FIG. 3B (Cont.)

```
                                                              ← CONSTANT REGION →
         I   F   G   T   L   L   S   V   K   P   N   I   Q   N   P   E   P   A   V   Y   Q   L   K   D   P   P   R   S   Q   D
        110                                                 120                                                 130
        ATC TTT GGA ACT CTG CTT TCT GTC AAG CCA AAC ATC CAG AAC CCT GAA CCT GCT GTG TAC CAG TTA AAA GAT CCT CGG TCT CAG GAC

S   T   L   ©   L   F   T   D   F   F   D   S   Q   I   N   V   P   K   T   M   E   S   G   T   F   F   I   T   D   K   T   V   L
                        140                                                 150                                                 160
        AGC ACC CTC TGC CTG TTC ACC GAC TTC TTC GAC TCC CAA ATC AAT GTG CCG AAA ACC ATG GAA TCT GGA ACG TTC TTC ATC ACT GAC AAA ACT GTG CTG
                                                                                                         CHO
                                                                                                 ┌─ N   Q   T ─┐                       ┌─ N
         D   M   K   A   M   D   S   K   S   N   G   A   I   A   W   S   N   Q   T   S   F   T   ©   Q   D   I   F   K   E   T   N
                        170                                                 180                                                 190
        GAC ATG AAA GCT ATG GAT TCC AAG AGC AAT GGG GCC ATT GCC TGG AGC AAC CAA ACA AGC TTC ACC TGC CAA GAT ATC TTC AAA GAG ACC AAC
        CHO
        ┌─ T                                                                                                                   ┌─ CHO ─┐
                                                                                                                                 ┌─ N   L   S
         A   T   Y   P   S   S   D   V   P   ©   D   A   T   L   T   E   K   S   F   E   T   D   M   N   L   N   F   Q   N   L   S
                        200                                                 210                                                 220
        GCC ACC TAC CCC AGT TCA GAC GTT CCC TGT GAT GCC ACG TTG ACC GAG AAA AGC TTT GAA ACA GAT ATG AAC CTA AAC TTT CAA AAC CTG TCA
                        TRANSMEMBRANE                                                                         CYTOPLASMIC
                        230                                                 240                                                 250
         V   M   G   L   R   I   L   L   L   K   V   A   G   F   N   L   L   M   T   L   R   L   W   S   S   ***
        GTT ATG GGA CTC CGA ATC CTC CTG CTG AAA GTA GCG GGA TTT AAC CTG CTC ATG ACG CTG AGG CTG TGG TCC AGT TGA GGTCTGCAAGACTGACAGA

GCCTGACTCCAAGTTCCGTCCTCCACCCCTCCGCCTCCTCTTCAAGCAAAAGGAGCCGGCTGTCTGGGGTCTGTTGGCCCTGATTCACAATCCCACCTAGATCTCCCAGATTTGTGAG

GAAGGTTGCTAGAGAGCTAAGCGC
```

T CELL RECEPTOR BETA SUBUNIT

CROSS-REFERENCE TO RELATED APPLICATIONS

This application is a division of application Ser. No. 08/235,601, filed Apr. 29, 1994, now U.S. Pat. No. 5,840,304, which is a division of application Ser. No. 07/924,395, filed Aug. 3, 1992, now U.S. Pat. No. 5,316,925, which is a continuation of application Ser. No. 06/663,809, filed Oct. 22, 1984, now abandoned, which is a continuation-in-part of application Ser. No. 06/585,333 filed Mar. 1, 1984, now abandoned, the disclosures of which are incorporated hereby by reference in their entirety.

STATEMENT REGARDING FEDERALLY-SPONSORED RESEARCH

This invention was supported in-part by Grant No. AI19512 from the National Institutes of Health.

BACKGROUND OF THE INVENTION

1. Field of the Invention

The hematopoietic system is extraordinarily complex, which is not surprising in view of the central role blood cells play in the maintenance and survival of the host. One aspect of great importance is the manner in which the host protects itself from various pathogens. Two families of cells play a salient role in protecting the host, B-cells and T-cells. The mystery of how the B-cells are able to produce an extraordinary variety of immunoglobulins has been explained to a substantial degree. The germline DNA is now known to undergo rearrangements, so as to join various exons together to produce a variable region which is then joined to differing constant regions as the B-cell matures. The mechanism by which the DNA undergoes the rearrangement and the subsequent transcript is spliced to produce a messenger RNA coding for a specific immunoglobulin has been an exciting adventure demonstrating the potency of the tools afforded by the developments in molecular biology. Another class of cells important to the immune system of the host is the T-cells. These cells differ from the B-cells in that they do not secrete immunoglobulins, although they appear to have a similar range of antigenic specificities. Particularly, helper T-cells, which are involved in stimulating B-cell proliferation, can have specificity analogous to that of B-cells, with the additional requirement that they must also recognize self-major histocompatibility determinants simultaneously.

The specificity of T-cells can find application in a wide variety of situations. If one could modify a helper T-cell by introducing a foreign receptor site, one could change the response of the host to a foreign antigen. Furthermore, in many situations, it may be of interest to determine whether a cell is a helper T-cell or other type of cell. In addition, one has the opportunity to determine monoclonality in the host, which can be useful in the diagnosis of T-cell leukemias. Also, having DNA sequences which encode for portions of the T-cell antigen-specific receptor would allow for constructions involving the combination of native T-cell sequences with foreign sequences to produce novel proteins which could act as receptors. Also, antisera and monoclonal antibodies could be generated against specific parts of the protein, using either synthetic peptides or producing the protein in an expression vector. By employing hybridization with DNA sequences, subsets of T-cells may be determined as well as genetic differences and defects.

2. Description of the Prior Art

The second domain of HLA-DC has been shown to be homologous to immunoglobulin. Auffray et al., Proc. Natl. Acad. Sci. USA (1982) 79:6337–6341. The sequence about the intrachain disulfide bond in the immunoglobulin variable region is discussed by Kabat et al., in Sequences of Immunological Interest, U.S. Dept. of Health and Human Services, Washington, D.C. (1983). Cross-reactivity between B-cell anti-idiotypic antisera and T-cells is reported by Eichmann and Rajewsky, Eur. J. Immunol. (1975) 5:661–666; Binz and Wigzell, J. Exp. Med. (1975) 142:197–211, and Augustin et al., in Regulatory T Lymphocyte (eds. Pernis and Vogel) 171–184, Academic Press, N.Y., 1980. Lack of nucleotide sequence similarity between T-cell specific genes and immunoglobulin coding genes is reported by Kronenberg et al., J. Exp. Med. (1980) 152:1745–1761 and Kronenberg et al., ibid. (1983) 158:210–227, among others. Murine T-cell specific proteins are reported by Kappler et al., Cell (1983) 34:727–737 and McIntyre and Allison, ibid. (1983) 34:739–746. Allison et al., J. Immunol. (1982) 129:2293–2300; Haskins et al., J. Exp. Med. (1983) 157:1149–1169; Meuer et al., Nature (1983) 303:808–810 and Samuelson et al., Proc. Natl. Acad. Sci. USA (1983) 801:6972–6976 report the immunoprecipitation from T-cells of a disulfide linked heterodimer composed of two distinct glycoproteins of 37–50 kD in size. McIntyre and Allison, supra (1983) and Acuto et al., Cell (1983) 34:717–726 report that the heterodimer appears to have variable and constant portions by peptide map analyses. Heber-Katz et al., J. Exp. Med. (1982) 155:1086–1099 and Hedrick et al., Cell (1982) 30:141–152 report the production of MHC-restricted T-helper hybridomas, which disclosure is incorporated herein by reference. Davis et al., in B and T Cell Tumors, UCLA Symposium Vol. 24 (eds. Vitteta and Fox) 215–220, Academic Press, N.Y. 1982, report that T and B lymphocytes differ by a very small fraction of their gene expression.

Saito, Nature (1984) 309:757–762, reports a T-cell-specific cDNA clone which is rearranged in cytotoxic T-cell DNAs and has variable, constant and joining region homologous elements. Siu et al., Cell (1984) 37:393–401 and Kavaler et al., Nature (1984) 310 421–423, report the presence of diversity elements in the β-chain. The α-chain of T-cell receptor molecules has been reported to be as diverse as the β-chain (Kappler et al., Cell (1983) 35:295–302).

SUMMARY OF THE INVENTION

A technique is provided whereby rare messenger RNA is isolated. By means of this technique, DNA sequences encoding for antigen-specific receptors in T-cells are obtained as well as other T-cell specific gene products. The DNA can be used in a variety of ways, such as nucleotide probes, combining with foreign DNA sequences to produce novel T-cell receptors, which can be used in an analogous manner as antibodies, or constructs can be provided which provide for extrachromosomal elements or integration into a host genome, where the hybrid proteins may be expressed and transported to the membrane.

BRIEF DESCRIPTION OF THE DRAWINGS

FIG. 2 shows the complete nucleotide sequence of 86T1 (Seq. ID no. 1) and partial sequences of the other cDNA clones (86T3: Seq. ID no. 3; 86T5: Seq. ID no. 5; TM86: Seq. ID no. 7), indicating the 5'-untranslated region (UT), the leader polypeptide, variable, joining, and constant regions, with the numbering following the amino acid sequence of 86T1 (Seq. ID no. 2) and possible carbohydrate attachment sites (CHO) (N-X-S or N-X-T) noted.

FIG. 3A shows the sequencing strategy of TT11 cDNA clones, with thin lines indicating 5'-end labeling with polynucleotide kinase and thick lines indicating 3'-end labeling with the Klenow fragment of DNA polymerase I.

FIG. 3B also shows the nucleotide sequence (Seq. ID no. 9), predicted amino acids (Seq. ID no. 10), and indicates generally the individual regions. "TCHO" indicates potential signal sequences for N-linked glycosylation.

DETAILED DESCRIPTION

Figure 1:
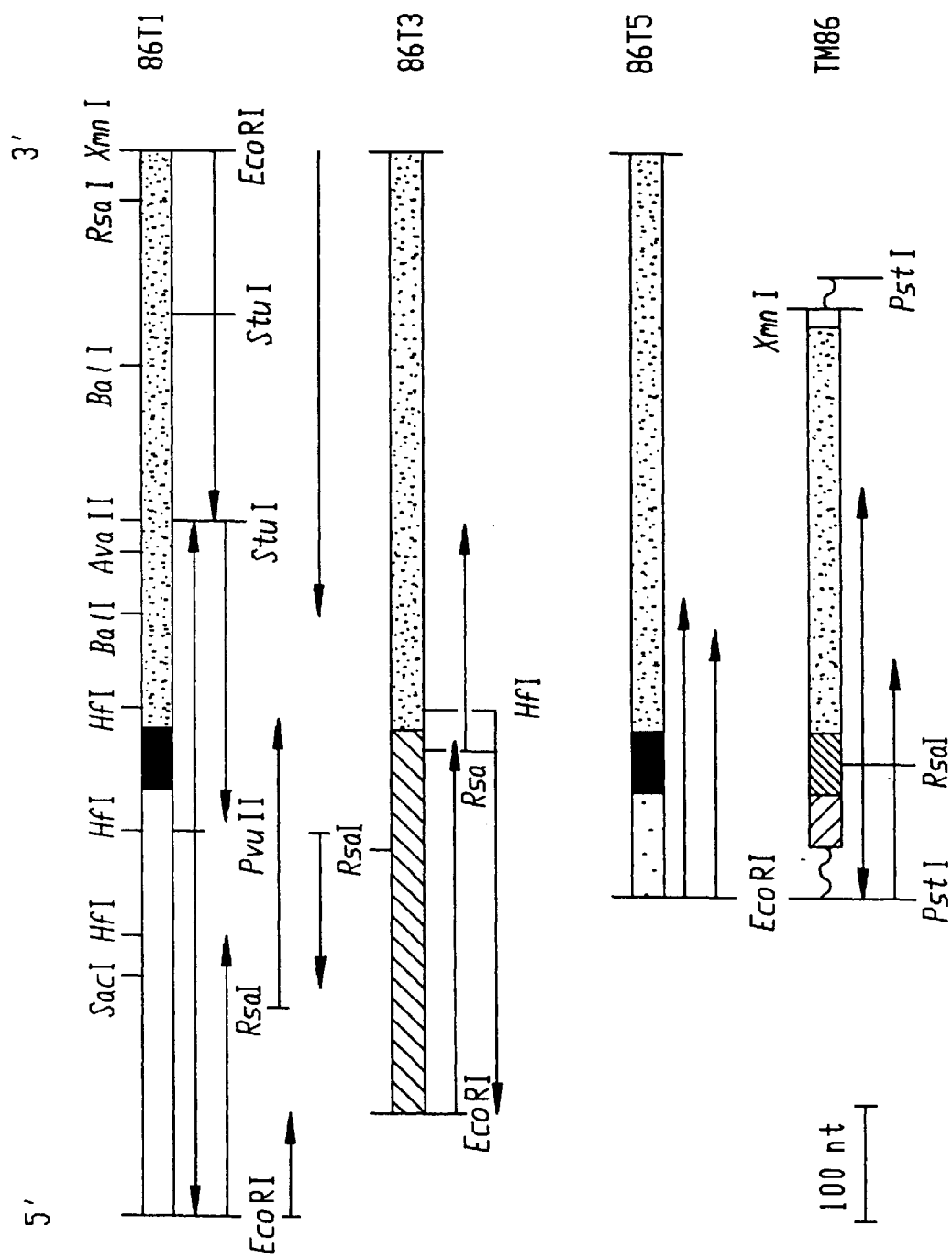
FIG. 1 is a restriction map of T-cell antigen receptor fragments, where shaded areas indicate major homologies between the different cDNA clones. Sequencing was by the procedure of Maxam and Gilbert, Proc. Natl. Acad. Sci. USA (1977) 74:560, with thick arrows representing 3'-end labeling (Klenow) and the arrows 5'-end labeling (polynucleotide kinase).

In accordance with the subject invention, novel DNA sequences are provided involving in-whole or in-part coding sequences for antigen-specific T-cell receptors or fragments thereof, specifically involving functional regions, which may be found on one or more exons in the germline and rearranged DNA or in-whole or in-part as cDNA from a mature messenger RNA.

The mammalian T-cell receptors appear to be 80–90 kdal heterodimers, which are disulfide linked, and composed of two distinct glycoproteins of about 40 to 50 kD (kilodaltons), referred to as the α- and β-subunits. The two glycoproteins have variable and constant regions or domains by peptide map analysis.

The DNA sequences encoding for the glycoproteins of the heterodimer are divisible into variable, joining and constant regions, analogous to immunoglobulins, as evidenced by the sequences having significant homology with the immunoglobulin sequences and by the independent assortment of the J-like elements. Each of the subunits appears to have diversity (D) regions comparable to the heavy chain of immunoglobulins.

The α- and β-subunits have many similarities between themselves, other T-cell membrane proteins and immunoglobulins or B-cell receptor proteins. For the most part, the overall homology is low with few similarities of either amino acid sequence or nucleotide sequence in the constant regions. (The methionine of the leader peptide will be used as 1 for the amino acid sequence.) The cysteine spacing is found to be between about 65 to 70 amino acids in the variable region (α-65; β-69; Igλ or κ-65). In addition the sequence "WYRQ" (Seq. ID no. 11) in the variable region of the α-chain at about residue 55 finds analogy in the β-chain in "WYKQ" (Seq. ID no. 14) and analogous sequences at comparable positions in immunoglobulins. In the variable regions, the sequence "DSA-Y-CAV" (Seq. ID no. 12) is found in the region of residues of about 100–115, with one or two differences in amino acids.

The J region appears to be the most highly conserved with 7 of 16 residues of the α-chain the same as the β-chain and significant homology with consensus sequences of murine heavy and light chains.

Also characteristic of the T-cell receptor sequences is the sequence "ILLXK" where X is L (Seq. ID no. 13) or G (Seq. ID no. 15), having a basic amino acid in the transmembrane region.

In support of a D or diversity region, 5' to the "SGN" sequence at about residues 115 to 120, is the nucleotide sequence "$G_5$". In 7 of 14 β-chain putative D regions, runs of "$G_{3-7}$" are found on the 3'-side, which finds analogy in immunoglobulin heavy chain D regions.

The α- and β-chains are encoded in germline DNA which is subject to rearrangement to provide a transcript which may be further processed. Either the genomic DNA may be used or cDNA from the mature transcript for purposes described hereinafter.

Each of the chains has from 3 to 5, usually 4 to 5 N-glycosylation sites, where some or all of them may be employed.

The two chains of the heterodimer are different and appear to be derived from different gene loci. The sequences for a β-chain (Seq. ID no. 1) and an α-chain (Seq. ID no. 9) are set forth in FIGS. 2 and 3B, respectively. The chains may be divided up into regions associated with specific exons by analogy to immunoglobulins. The primary regions are the leader region, variable region (V), diversity region (D), which may be part of V, the joining region (J), the constant region (C), the transmembrane region (TM) and the cytoplasmic region (Cy).

The αchain without glycosylation will be about 25 to 30 kD (kilodaltons), while the β-chain will be about the same or larger, being about 25 to 35 kD. With glycosylation the subunits will be about 35 to 50 kD each, usually 40 to 50 kD each, providing a sulfhydryl linked heterodimer of 80 to 90 kD.

For each of the subunits, the rearranged DNA in helper T-cells, including introns will generally be approximately 6 to 8 kbp, with individual exons being substantially smaller and approximating the size of cDNA sequences for domains plus whatever flanking regions are included.

The DNA sequence coding for the constant region (including the transmembrane and cytoplasmic region) will generally be about 400 to 600 nt (nucleotides), plus about 300 nt of 3' untranslated regions. These sequences will be characterized by having codons encoding for intrachain disulfide linkages between cysteines spaced apart about 100 to 200 nt, usually about 100 to 150 nt.

In conjunction with the constant region is a probable transmembrane sequence, primarily including hydrophobic amino acids and having from about 45 to 105 nt. This sequence will define the 3'-terminus of the constant region and may include about 5 to 15 codons (15 to 45 nt) for amino acids which extend into the cytoplasm of the cell.

The next region or domain which appears to have functional significance is the region analogous to the J region of immunoglobulins. As is known with immunoglobulins, there are a plurality of J regions, adjacent to a given C region ranging about 1 to 6 in number, more usually about 4 to 5. The J regions encode about 15 to 20 amino acids, the β-chain with 16 amino acids having greater similarity to the immunoglobulin heavy chain J regions, in that the heavy chain J regions are typically 17 amino acids, while the light chain J regions are typically 13 amino acids.

The J regions can be used in conjunction with constant regions which may or may not include the transmembrane sequence and cytoplasmic sequence to be joined to other DNA sequences, e.g., non-wild sequences, to produce hybrid sequences to allow for novel hybrid proteins on T-cell surfaces. (By "non-wild" is intended a sequence other than the wild-type or native sequence, while "foreign" intends from a source which does not normally exchange genetic information with the source of the T-cell antigen receptor DNA sequence.)

In order to have the hybrid proteins transported to the surface, the secretory leader sequence present with the T-cell antigen receptor is employed as the 5'-terminus. The sequence is of about 15 to 25 amino acids, more usually 18 to 24 amino acids. Thus constructs can be prepared, where various domains of the T-cell antigen receptor DNA sequence, which may include non-coding flanking regions, are separated by non-wild type DNA.

Novel DNA constructions can be employed for cloning and/or expressing the T-cell antigen receptor, individual subunits, fragments thereof, or combinations of fragments with non-wild DNA, including foreign DNA, to produce hybrid proteins. The fragments will be of at least about 15 nt, usually at least about 50 nt. These constructions will for the most part have the following formula:

$$(RS)_a\text{-}(M)_b\text{-}(tis)\text{-}(eis)\text{-}(T\text{-}AgR)\text{-}(ets)\text{-}(tts)$$

wherein:

"RS" indicates a replication system which may be derived from prokaryotes or eukaryotes, plasmids, phage, or viruses, where one or more replication systems may be involved which allow for replication in different hosts, e.g., unicellular microorganisms, and maintenance as extrachromosomal elements; illustrative replication systems or vectors include lambda, simian virus, papilloma virus, adenovirus, yeast 2 m$\mu$ plasmid, ColEI, pRK290, pBR322, pUC6, or the like, where the replication system may be complete or may be only a partial replication system, interacting with a helper plasmid or one or more genes present in the genome, e.g., COS cells; for cloning, a replication system will be employed, such as a plasmid or viral replication system recognized by the unicellular host, for example, bacteria, yeast, etc., particularly E. coli;

"a" is an integer of from 0 to 3, usually 1 to 3, being 0 where integration into the chromosome is desired, although integration can be achieved with native or foreign replication systems;

"M" intends a structural gene or cistron, referred to as a marker, with its transcriptional and translational regulatory signals which provides means for selecting host cells which contain the construct; markers include biocide resistance, such as resistance to antibiotics, e.g., ampicillin, chloramphenicol, neomycin, G418, or the like, toxins, heavy metals, etc.; immunity; complementation providing prototrophy to an auxotrophic host, or the like;

"b" is an integer of from 0 to 3, more usually 0 to 2, preferably 1 to 2;

"tis" intends the transcriptional initiation sequences for regulating transcriptional initiation and includes one or more promoters, including the native promoter by itself or in combination with other promoters, e.g., viral promoters or foreign promoters, as well as sequences which affect the promoter, such as operators, activators, enhancers, capping sequence, TATA and CAAT sequences, or the like, where the sequences will be organized in the construct so as to be able to fulfill their function;

"eis" intends the expression initiation sequences for regulating expression and includes any ribosomal binding site, the initiation codon as appropriate, oligonucleotides separating the ribosomal binding site and initiation codon, where such sequences affect expression, and the like;

"T-AgR" intends the T-cell antigen receptor or a hybrid DNA sequence comprising fragments of the T-cell antigen receptor and hybrid DNA sequences, where the sequences together provide for an open reading frame coding for the antigen receptor or hybrid protein;

"ets" intends expression termination sequences, which may include one or more stop codons and such other sequences as may be appropriate; and "tts" intends transcriptional termination sequences, which may include the transcriptional terminator, normally balanced with the transcriptional promoter and may be one or more terminators in combination with one or more stop codons, polyadenylation signal sequence, or the like.

The T-cell antigen receptor subunit or hybrid T-cell antigen receptor will for the most part have the following formula:

$$(S.L.)_c\text{-}(V\text{-}seq)\text{-}J\text{-}C\text{-}(TM)_d\text{-}(Cy)_e$$

wherein:

"S.L." intends a secretory leader sequence, which will encode for about 15 to 25 amino acids, more usually about 17 to 24 amino acids, and preferably about 19 to 23 amino acids having 45 to 75 nt, usually 51 to 72 nt, preferably 57 to 69 nt;

"c" is 0 or 1;

"V-seq" intends a DNA sequence which encodes for the variable region of the T-cell antigen receptor subunit or may be replaced by a sequence encoding for a different polypeptide, which DNA sequence will be in reading frame with the secretory leader sequence (S.L.) as appropriate or may have its own initiation codon in the absence of the secretory leader sequence; the variable sequence will generally be at least about 60 nt and not more than about 600 nt, more usually not more than about 400 nt; where the sequence codes for a T-cell receptor variable region, the sequence will generally range from about 270 to 330 nt, more usually from about 285 to 312 nt;

"J" intends the joining region and will generally be from about 42 nt to about 60 nt, more usually from about 45 nt to 57 nt, and frequently about 48 to 54 nt, where the J region will be selected from a limited number of sequences associated with the joining region exons of the T-cell antigen receptor subunit;

"TM" intends the transmembrane integrator sequence which will be a hydrophobic sequence of from about 51 to 90 nt, more usually from about 84 to 96 nt;

"d" will be 0 or 1;

"Cy" intends the sequence extending from the membrane into the cytoplasm, which will normally be from about 12 to 30 nt, more usually from about 15 to 24 nt, particularly about 15 to 18 nt; and "e" is an integer from 0 to 1.

Each of the two subunits, $\alpha$- and $\beta$-, may be expressed independently in different hosts or in the same host. Where the two subunits are expressed in the same host, depending upon whether a microorganism host or mammalian host is employed will affect the processing of the subunits and assembling of the subunits into the T-cell receptor. Involved with processing is folding, glycosylation, transport through the endoplasmic reticulum and Golgi apparatus, cleavage with removal of the secretory leader sequence, as well as capping or blocking of the N-terminus by acetylation. As part of the processing or independent of the processing folding of the subunits and assembling of the subunits into the T-cell receptor must occur. With mammalian cells, it is to be expected that the resulting protein will substantially conform with the naturally occurring T-cell receptor in its chemical, physical and biological properties. However, with lower eukaryotes and prokaryotes, various of the process steps may occur in whole or in part, differently or not at all. Therefore, the sequences may be modified by replacing the wild type secretory leader sequence with a secretory leader sequence recognized by the expression host or provide for an initiation codon at the beginning of the variable region.

The subunits may then be isolated in the cytoplasm and the receptor formed by bringing the α- and β-subunits together under renaturing conditions.

DNA coding for receptor subunit fragments should encode for a polypeptide of at least 8 amino acids, usually at least 15 amino acids (24 nt and 45 nt, respectively), so as to provide polypeptides having biological activity, e.g., immunological.

The constructions, as indicated, can be prepared by inserting DNA coding for only a portion of a T-cell antigen receptor subunit where the vector has one or more appropriate restriction sites, or can be modified, for example, by adapters, to provide for insertion at an appropriate site in relation to a promoter and associated regulatory sequence, e.g., RNA polymerase binding site for transcription and to appropriate translational regulatory sequences, e.g., ribosomal binding site, or to be in reading frame with a leader sequence.

The domains or regions of the T-cell antigen receptor can be employed individually or in combination. By employing cDNA, one can obtain the gene in open reading frame coding for the preprotein, that is the protein prior to processing, such as removal of the secretory leader, glycosylation, or the like. By restriction mapping the cDNA, one can determine the presence of convenient restriction sites adjacent the borders between the individual domains as indicated in the above formula. Where a restriction site is not at the border, one can still cleave at a site near the border, using either partial or complete digestion as appropriate with the appropriate restriction enzyme. Where nucleotides have been removed so as to have a truncated sequence, one may replace the nucleotide(s) employing appropriate adapters which allow for joining the domain of interest to another nucleotide sequence in proper reading frame. Where extra nucleotides are present, one can remove these by resection, e.g., employing Bal31, by primer repair, or the like. Alternatively, where there is degeneracy in the codon for a particular amino acid, in vitro mutagenesis may be employed to modify one or more nucleotides which would then provide the proper recognition sequence for a restriction enzyme. These techniques have been extensively described in the literature and do not require exemplification here.

The DNA sequences which are employed, may be the same or different from the sequences isolated in accordance with the subject invention. By employing the J or C domain sequences either by themselves or in combination with other sequences, e.g., transmembrane sequences, the subject sequences can be used as probes for determining the presence of homologous sequences in the same or different species and for isolating sequences having equivalent functions. In this manner, a repertory of sequences can be obtained which can be joined together to provide for a variety of cistrons coding for T-cell antigen receptors or hybrid proteins employing varying combinations of fragments from T-cell antigen receptors.

By joining the secretory leader sequence of the T-cell antigen receptors to a non-wild DNA sequence, one can provide for secretion of a hybrid protein into the nutrient medium and processing, so as to obtain a mature protein product from a mammalian host. Where the protein is a eukaryotic protein, it can be properly processed, so as to provide a product which is the same or substantially the same as the naturally-occurring eukaryotic protein. Alternatively, if one wishes to provide for specific proteins on the T-cell surface or surface of a different mammalian cell, one can interpose the foreign sequence coding for the foreign protein between the secretory leader sequence and the transmembrane sequence in place of the sequences coding for the variable, J and constant regions of the T-cell antigen receptor subunit. In this way, one can provide for a totally different surface membrane protein at the cell surface, modifying the surface characteristics of the cell.

By using the expression products of the subject constructs, one can obtain antibodies to the expression products, which can then be used for detecting the presence of T-cell antigen receptors or individual subunits, due to sharing idiotypic determinants or common determinants to the J or C regions.

The cloned DNA sequences, particularly of the sequences extending from the 5'-end of the C region to the 3'-end of the cytoplasmic region can be used as probes. Usually, the probes will be at least about 15 nt, more usually at least about 30 nt and will generally not exceed 1500 nt, more usually not exceeding about 1000 nt, preferably not exceeding about 500 nt of homologous sequence. Additional, non-homologous flanking sequences may be present which may be up to 5 knt or more.

The nucleotide sequences employed as probes may be RNA or DNA and may be labeled in a wide variety of ways. Commonly, probes are labeled with $^{32}$P and may be detected by autoradiography. Alternatively, biotin, novel sugars, or any other molecule may be included by virtue of the use of synthetic techniques for producing the oligonucleotide. Thus, any terminal group may be introduced in a simple manner to act as a source of a detectable signal. These groups may be introduced directly or indirectly, that is, by covalent bonding, ligand-receptor bonding, e.g., haptens and antibodies, or the like. Illustrative labels which provide for a detectable signal include fluorescers, chemiluminescers, enzymes, radioactive labels, magnetic particles, and the like.

Two different methods for obtaining rare messenger RNA were employed for isolating the rare messenger RNAs associated with the T-cell antigen receptor subunits. The method employed for the β-subunit involved the separation of membrane-bound polysomal RNA from non-membrane-bound RNA. The membrane-bound polysomal fraction of RNA was then reverse transcribed to produce single-stranded (ss) cDNA. The cDNA was then labeled with $^{32}$P and repeatedly hybridized with B-cell mRNA and fractionated on hydroxyapatite. Remaining ss cDNA which passed through the column was isolated. A second T-helper hybridoma was then used to prepare a cDNA library and was screened with the cDNA probes prepared from the first T-helper hybridoma. This resulted in substantial enrichment for T-cell-specific membrane associated sequences (about 200-fold).

The reduced number of selected clones was rescreened using the initially prepared probes. The positive clones were then nick-translated and hybridized to B-cell mRNA under Northern blotting conditions. Those clones that did not hybridize to the B-cell mRNA's were selected as T-cell-specific.

The clones were then employed to investigate somatic rearrangements as follows. Those which hybridize to RNAs having greater than 1000 nt were hybridized to Southern blots of genomic DNA from various sources including a helper T-cell hybridoma and a thymoma. The DNAs were prepared by standard methods, digested with a particular restriction enzyme, in this case, PvuII, electrophoresed through 0.9% agarose and blotted on to nitrocellulose. Moderate to strict stringency was employed, and both the thymoma and hybridoma were found to give substantially different patterns from the other non-T-cell DNA.

The method employed for the α-subunit involved a variable-region specific subtracted cDNA probe between T-cells of differing specificities. Random-primed labeled cDNA from the mRNA of a helper hybridoma was synthesized. After fragmentation to an average size of about 300–400 nt, sequences were subtracted with mRNA from at least two different T-helper hybridoma or T-helper like lymphoma line, using hydroxyapatite to separate single from double-stranded nucleic acid. The single-stranded cDNA remaining was then hybridized to a cDNA library prepared from the cell line providing the original cDNA. Further elimination of irrelevant sequences can be achieved by rescreening the positive clones with oligo-dT primed cDNA from the same T-helper hybridoma, where the cDNA is reverse transcribed from membrane bound polysomal mRNA subtracted with mRNA from a macrophage or other lymphocytic line. Resulting hybridizing clones are found to be related to the variable region of the T-cell receptor.

By employing hybrid DNA technology the α- and β-subunits can be prepared individually or combined as a receptor having high specificity and affinity for specific conformations of organic molecules, such as polypeptides, polysaccharides, lipids, haptens and combinations thereof. A class of receptors is provided analogous to the immunoglobulins which can be used in substantially the same way, but lacking properties associated with immunoglobulins, such as Fc determinants, complement associated cytotoxicity, or other characteristics specifically associated with immunoglobulins. The subject receptors can be used to compete with surface membrane bound T-cell receptors in vivo in blood to inhibit proliferation of helper cells activated by the homologous antigen.

The T-cell receptors may be used in most of the situations where immunoglobulins find use, such as diagnostic assays, affinity chromatography, site-directed therapy or diagnosis where the T-cell receptor may be conjugated directly or indirectly to radionuclides, nmr active compounds, fluorescers, toxins, e.g., abrin, ricin, etc., or the like.

By having the genes available for the α- and β-chains, the chains and, therefore, the receptors may be prepared in large amounts from cells other than human cells, which are less fastidious in their growth requirements than human cells. The T-cell receptors may be prepared in bacteria, e.g., *E. coli, B. subtilis,* etc., eukaryotes, e.g., yeast, filamentous fungus, murine cells, etc.

The following examples are offered by way of illustration and not by way of limitation:

EXPERIMENTAL

The procedure for gene isolation of genes encoding for helper T-cell antigen-specific receptor subunits α- and β- ($T_H$-Ag receptor, α- or β-subunit) is as follows.

The isolation of the β-subunit will be considered first. Membrane-bound T-helper cell cDNA probes was subtracted with B-cell messenger RNA and used to screen a cDNA library which was the product of another $T_H$-B-cell lymphoma combination. The library was constructed as described below for a B-cell-specific library (Davis et al., Proc. Natl. Acad. Sci. USA 81(7): 2194–2198 (1984)) and by a similar procedure for xenopus embryonal stage specific library (Sargent and Dawid, Science (1983) 222:135–139) using $T_H$-hybridomas M12 or 2B4 (Hedrick et al., Cell (1982) 30:141–152). The B-cell mRNA was obtained from the B-cell lymphomas L10A and Ba117 (Kim et al., J. Immunol. (1979) 122:549–554). The cDNA was $^{32}$P-labeled for detection. The $T_H$-B library was 20-fold enriched for T-cell-specific sequences as judged by the fact that 95% of the mass of the cDNA was removed in the subtraction at the hydroxyapatite stage.

The exemplary procedure for the B-cell library follows. The cell lines Ba117, B-cell lymphoma (IgM$^+$ IgD$^+$ Ia$^+$) (Kim et al., J. Immunol. (1979) 122:549–554) and Ba14, T-cell thymoma (Thy1$^+$ Lyt1$^-$ Lyt2$^+$ TL$^+$) (Kim et al., ibid. (1978) 121:339–344) were grown in RPMI, glutamine, 70% fetal calf serum and 5×10$^{-5}$ M β-mercaptoethanol in a 5% $CO_2$ atmosphere. After growing to a high density (1–2×10$^6$/ml) refreshed with new media for 2 to 4 hr, the cells were chilled with PBS and harvested. The cells were washed several times in cold PBS, resuspended in 0.14M KCl, 0.02M Tris, pH 8.0, 0.0015M $MgCl_2$, lysed with the addition of NP-40 to 1% and the nuclei pelleted. The cytoplasmic fraction was made 0.5% SDS, 5 mM EDTA and extracted 2–3× with saturated precipitated with ethanol (Mushinski et al., Proc. Natl. Acad. Sci. USA (1980) 77:7405–7409) and the polyA$^+$ RNA selected on oligo-dT cellulose (1–2 passages).

cDNA from the B-cell lymphoma was synthesized from 1 to 5 μg template polyA$^+$ RNA in 50 mM Tris, pH 8.3, 6 mM MgCl2, 70 mM KCl, 1 mM each dNTP, $^{32}$P-dCTP (o give first strand specificity of 10$^5$ cpm/μg), 10 μg/ml oligo-dT, 20 mM dithiothreitol, 100 μg/ml Actinomycin "D" in a 100 μl reaction mixture. Ten units AMV reverse transcriptase was added per μg polyA$^+$ RNA and incubated for 2 hr at 42° C. After adding an equal volume of 0.2M NaOH, the mixture was incubated at 70° C. for 20 min, cooled on ice, neutralized with 1M HCl and sodium acetate (pH 6.5) and SDS added to 0.2M and 0.1%, respectively. At room temperature, the cDNA was excluded from G-50F Sephadex in a Pasteur pipette column with a running buffer of 100 mM NaCl, 50 mM Tris, pH 7.5, 1 mM EDTA and 0.02% SDS. Fifty μg of tRNA was added as carrier and the cDNA precipitated in a silanized Eppendorf tube (1.5 ml). The precipitate was washed once with 70% ethanol, dried and resuspended in 0.5M phosphate buffer, 5 mM EDTA, 0.1% SDS and hybridized in sealed glass capillaries with the T-cell thymoma RNA at a 10-fold excess at 1 to 1.5 mg/ml. To absorb repetitive sequences, sheared mouse genomic DNA (1.2 mg/ml, 10 μg per reaction) was included. After boiling for 60 sec, the mixture was incubated for 16 to 20 hr at 60° C. Hydroxyapatite chromatography was then used to fractionate the material in 0.12M phosphate buffer, 0.1% SDS, 600° C.

The single-stranded fraction was made double-stranded with DNA polymerase I (Klenow fragment), trimmed with S1 nuclease and G-C tailed into the PstI site of pBR322. The plasmids were then cloned into *E. coli* at high efficiency (50–400×10$^3$ μg/insert) with an average insert size about 500 nt.

The library of 5000 selected clones was screened and rescreened by standard procedures (Maniatis et al. in Molecular Cloning, Cold Spring Harbor Press, Cold Spring Harbor, 1982) using the membrane-bound T-helper cell cDNA probes from the T-hybridoma 2B4 from which sequences common to B-cell messenger from the B-cell L10A had been subtracted (MBT$_{2B4}$–B$_{L10A}$). Thirty-five definite positives resulted, which was about 10% of the library. In order to determine which were derived from the same gene and which were different, as well as to remove only false positives, each of these plasmid clones was nick-translated and hybridized to representative Northern blots. Five were reactive with B-cell mRNA and the remaining 30 fell into one of the 10 distinct patterns of mRNA size and expression shown in the following Table.

TABLE

| Clone | Insert Size | Message Size | Expression Pattern* T-hybridoma | T-lymphoma | B-lymphoma |
|---|---|---|---|---|---|
| TM4 | 0.7 | 1.5,1.9 4.5 kb | + | + | − |
| TM8 | 0.8 | 1.9 kb | + | + | − |
| TM26 | N.D. | 1.0 kb | + | N.D. | − |
| TM28 | 0.8 | 1.6 kb | + | + | − |
| TM29 | N.D. | 0.6 kb | + | − | − |
| TM30 | N.D. | 0.7 kb | + | + | − |
| TM33 | N.D. | 1.7,1.9 3.0 kb | + | + | − |
| TM86 | 0.6 | 0.7 kb | + | + | − |
| TM90 | 0.25 | 1.7 kb | + | + | − |
| TM97 | 0.95 | 1.8,1.9 kb | + | + | − |

*T-hybridoma, 2B4 and C10; T-lymphoma, Ba14 and Bal13; B-lymphoma L10A and Bal17. −

TM8 cross-hybridized strongly with a rat thy-1 cDNA clone. thy-1 is a classic T-cell membrane antigen.

A cDNA library was now prepared from the hybridoma 3.3T (Heber-Katz et al., supra).

Each of the seven clones which hybridized to messengers of at least 1000 nt were labeled and hybridized to genomic Southern blots composed of DNA from the thymoma BW5147 (from the mouse strain AKR, Heber-Katz et al., supra), AKR liver, the antigen-specific T-cell 2B4 (a fusion of T-cells from B10.A mice with BW5147), and B10.A liver. The DNAs were prepared by standard methods (Maniatis et al., supra), digested with a restriction enzyme PvuII, electrophoresed through 0.9% agarose and blotted on to nitrocellulose. The autoradiograms from the Southern blots showed that except for the restriction polymorphism between AKR and B10.A seen with TM8 (thy-1), the patterns of hybridization with each clone were identical for all of the sources of DNA except in the case of TM86. There was a strikingly different pattern of PvuII fragments that hybridized to the clone from either BW5147 or 2B4, as compared to liver DNA from either of the parental strains. The clones which were surveyed were also hybridized to EcoRI and HindIII digests of genomic DNA and in each case only TM86 showed a significant difference between the T-cell DNAs and liver DNAs. The TM86 clone is PstI excisable from pBR322.

To test whether genomic rearrangements of a receptor gene were unique for T-cells of different antigen specificities, genomic blots consisting of DNA from five antigen-specific T-cell hybridomas were hybridized with a nick-translated insert from clone TM86. The results were that DNA from each of the antigen-specific T-cells yielded a unique pattern. Three different B-cell lymphoma tumor DNAs gave patterns identical to that of the liver indicating that the rearrangement appeared to be unique to the T-cells.

Also a series of cytotoxic lines express messenger RNAs similar to those of T helper cells (by cross-reaction with the gene described here) and also display rearrangement of their genomic DNA.

In order to obtain other cDNA clones which arose independently in different T-lymphocytes, a thymocyte cDNA library was prepared using the lambda vector gt10 (generally available from Ronald Davis, Stanford University, Stanford, Calif.). The library was screened with the TM86 clone using standard conditions (Maniatis et al. in Molecular Cloning (Cold Spring Harbor Press) Cold Spring Harbor, N.Y. (1982)). The library was constructed from total thymocyte polyA$^+$ RNA from young, Balb/C strain mice. The cDNA was prepared using AMV reverse transcriptase (Amersham). The cDNA was not methylated, accounting for cleavage within the mRNA sequence on the 3'-side. After filling in with DNA polymerase I, EcoRI linkers were joined to each end. The resulting fragments were then fractionated in the desired size range, and inserted into the single EcoRI restriction site located in the phage repressor gene of the lambda vector gt10. Introduction of a DNA fragment into the repressor gene produces cI$^-$ phage, which forms a clear plaque. The cI$^+$ phage forms a turbid plaque, allowing for selection of hybrid phage. To eliminate the parent phage from the gt10 libraries, the bacterial host utilized was $C_{600}$rk$^-$ mk$^+$ hfI, on which the parent phage forms plaques at very low efficiency. The cI$^+$ parent phage is suppressed, while the cI$^-$ hybrid phage plates normally.

Positively hybridizing recombinants were subcloned into the EcoRI site of pUC9 (Viera and Messing, Gene (1982) 19:259–268). Three thymus-derived clones were obtained designated 86T1, 86T3 and 86T5. A partial restriction map is shown in FIG. 1. The 86T series molecules all end at the same 3' position because of an internal EcoRI recognition site proximal to the 3' end of the coding sequence. The 5' end variation is presumably due to random chain termination during library construction.

Figure 2:
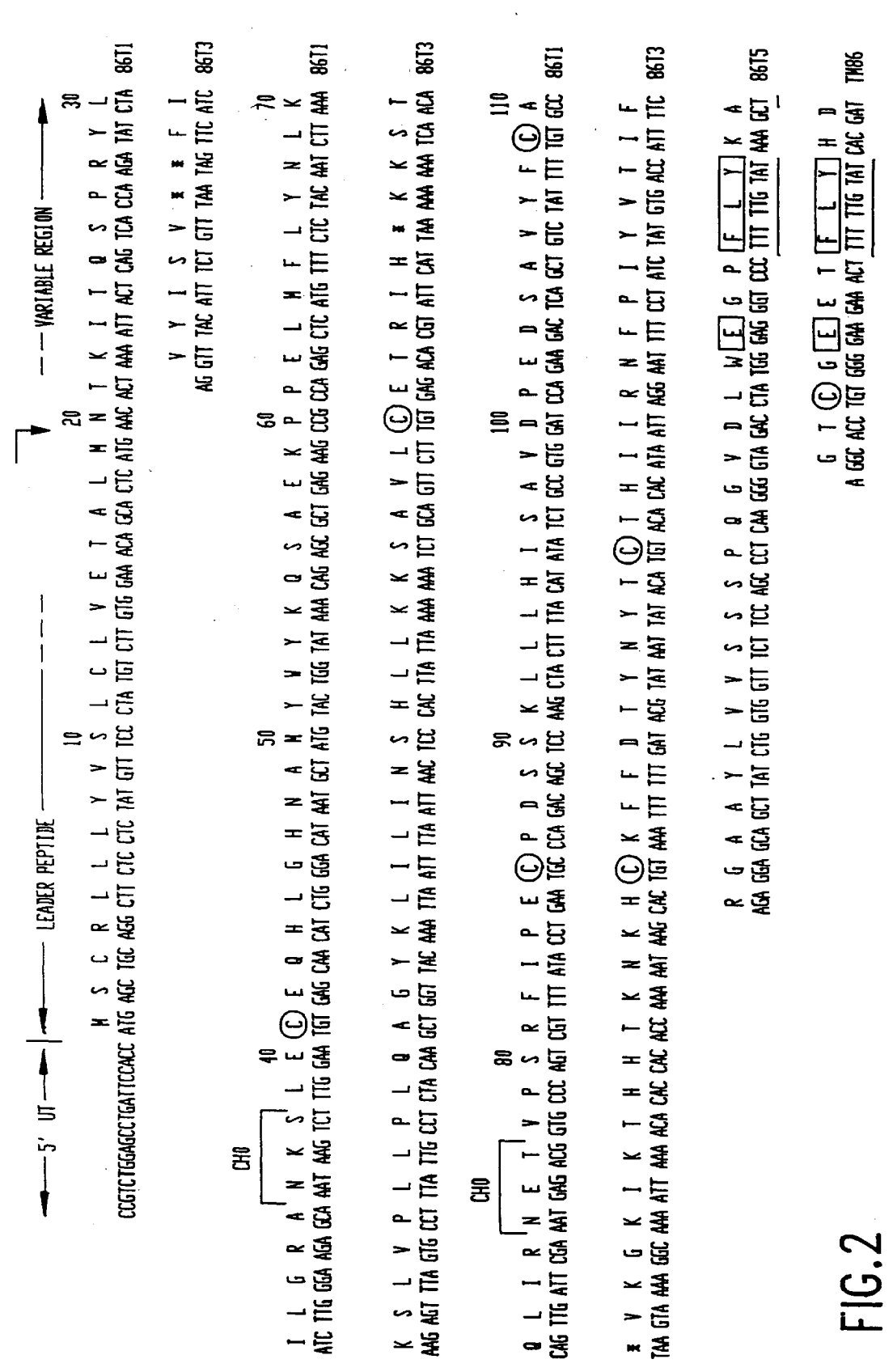
Figure 2:
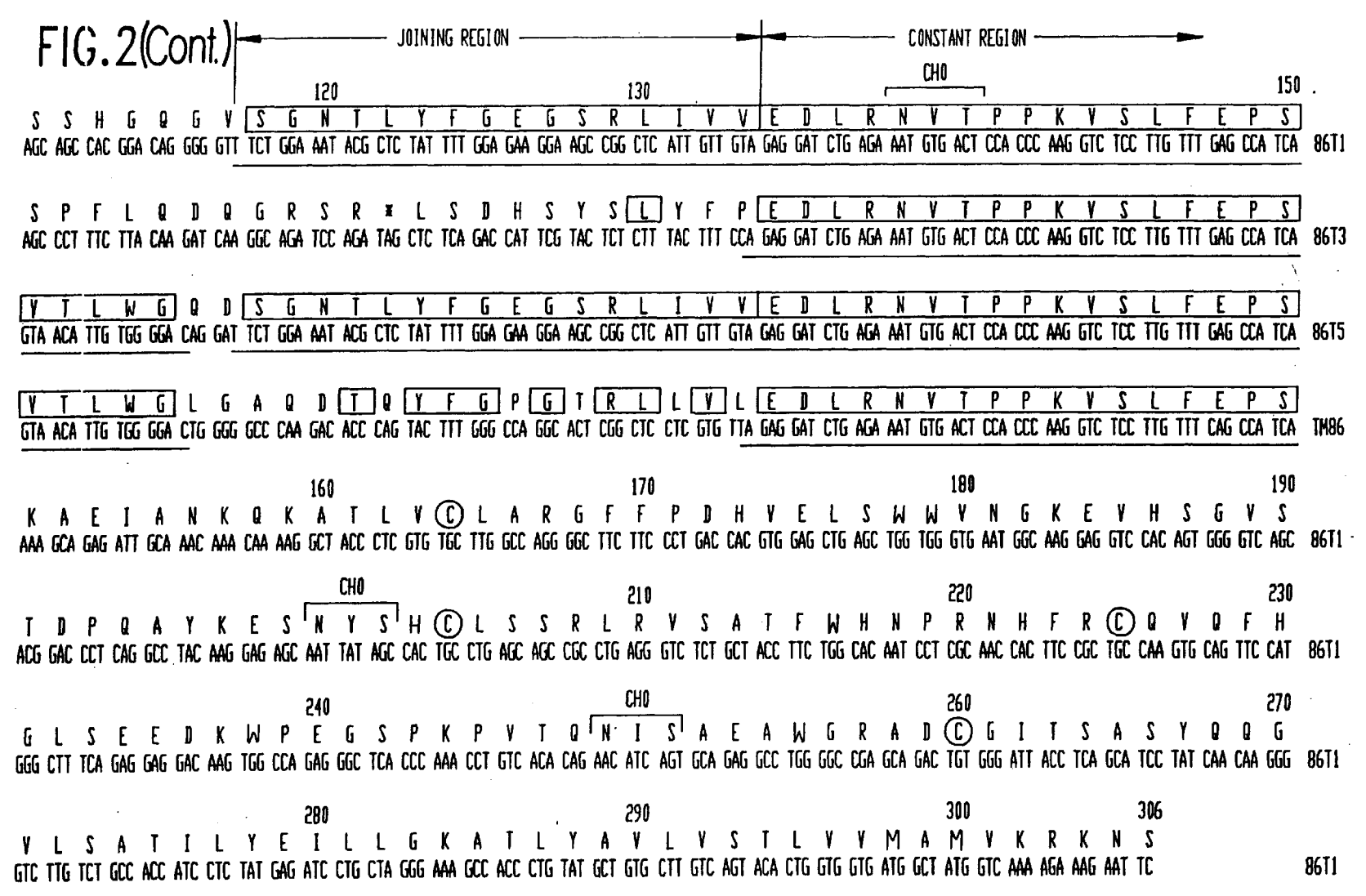

Based on the fact that the largest mRNA seen in Northern blots is 1300 nt, subtracting a polyA tail of 150–250 nucleotides gives an expected clone size of 1050–1150 nt. Therefore, it may be concluded that the 938 nucleotide size of 86T1 should contain most of the coding region sequence for a thymocyte molecule. 86T1 was completely sequenced and compared with the partial sequences of the other clones as shown in FIG. 2 (86T1: Seq. ID no. 1; 86T3: Seq. ID no. 3; 86T5: Seq. ID no. 5; TM86: Seq. ID no. 7).

Based on the comparisons a number of conclusions may be derived: (1) No two 5' ends are alike among the four cDNA clones, yet all have identical 3' ends, except as noted in FIG. 1. The entire constant region of 86T3 (Seq. ID no. 3) was sequenced and was found to be identical except for one nucleotide with that shown for 86T1 (Seq. ID no. 1). This 5' variable and 3' constant region structure is analogous to immunoglobulin cDNA clones. (2) There is a stretch of hydrophobic amino acids immediately following the methionine initiation codon corresponding to the expected leader polypeptide. In particular, the sequence Leu—Leu—Leu is common among kappa light chain leader polypeptides. (3) A 16 amino acid element between the variable and constant regions is shared at the nucleotide level between 86T1 (Seq. ID no. 1) and 86T5 (Seq. ID no. 5), but not with 86T3 (Seq. ID no. 3) or TM86(Seq. ID no. 7), suggesting an independently assorting J-like region. (4) Placement of cysteine and other residues suggests significant structural similarity to immunoglobulins and related molecules. (5) The apparent variable region of 86T3 (Seq. ID no. 3) appears non-functional because of the many (five) stop codons in frame with the otherwise normal constant region and, in fact, this clone has stop codons in reading frame, indicating that not all transcripts of this gene are successful in producing a viable molecule, at least in the thymus.

In order to analyze the sequence of this cDNA clone for evolutionary relationships with known proteins, the derived amino acid sequence was compared to the Dayhoff protein sequence data bank using the rapid comparison programs of Wilbur and Lipman, Proc. Natl. Acad. Sci. USA (1983) 80:726–730. From the Dayhoff bank of approximately 2300 sequences, the homologies of 25 sequences were greater than or equal to five standard deviations from the mean homology of the data bank. Of these 25 sequences, 24 were immunoglobulin constant or variable region sequences and one was a Class II human histocompatibility molecule. Furthermore, matches in the variable portion of 86T1 (Seq. ID no. 1) are with variable regions of immunoglobulins while those in the constant portion are with constant regions of immunoglobulin. Of 18 invariant residues in mouse kappa variable regions (Kabat et al., supra), 13 are present in the sequence of 86T1 (Seq. ID no. 1) and of the ten invariant residues of the heavy chain variable regions, six are present in 86T1 (Seq. ID no. 1). The spacing between the cysteine residues which form the disulfide loops of immunoglobulin variable regions is typically 65 amino acids for both kappa and lambda light chains and 70 amino acids for those of the heavy chains. The distance between the outermost two cysteines of the 86T1 (Seq. ID no. 1) variable region is an intermediate 68 amino acids. The alignment of the different immunoglobulin V regions predicts that the leader peptide of 86T1 (Seq. ID no. 1) will be cleaved just before the asparagine at position 20.

Pronounced homology was observed to immunoglobulins throughout what is probably the first constant region domain, particularly around the cysteine at position 164. In this region it was interesting to note that the sequence immediately 5' to the cysteine is homologous to light chains and the sequence 3' to heavy chains. Substantial homology is also observed to both kappa and lambda light chains around the last cysteine (position 260) in the 86T1 (Seq. ID no. 1) sequence.

Of the four clones, 16 amino acids are shared between the 86T1 (Seq. ID no. 1) and 86T5 (Seq. ID no. 5), but not with the other two clones sequenced, 86T3 (Seq. ID no. 3) and TM86 (Seq. ID no. 7). This homology falls precisely into the region occupied by joining (J) region elements in immunoglobulins. The putative J region of both 86T1 (Seq. ID no. 1) and TM86 (Seq. ID no. 7) show substantial homologies with all the immunoglobulin J regions. In terms of size, the putative J regions are more related to heavy chains (which average 17 amino acids) than light chains (13 amino acids).

In addition to the J element, the adjacent 5' region between amino acids 103–115 has substantial homology between 86T5 (Seq. ID no. 5) and TM86 (Seq. ID no. 7). In particular the 17 nucleotide and nine nucleotide identities between these two cDNA clones suggest other possible "mini-gene" elements possibly analogous to the D region of heavy chain immunoglobulins. Alternatively, these homologies may represent some highly conserved areas of related variable region genes.

A hydropathicity plot (Kyte and Doolittle, J. Mol. Biol. (1982) 157:105–132) was performed and indicated that: The 86T1 (Seq. ID no. 1) molecule has the alternating hydrophobic-hydrophilic stretches characteristic of globular proteins; the predicted leader polypeptide occurs in a hydrophobic environment; a transmembrane spanning region is indicated at the end of the 86T1 (Seq. ID no. 1) sequence, followed by a string of positive charges (lys-arg-lys), characteristic of the cytoplasmic portion of a number of lymphocyte cell-surface markers.

In conclusion, the structure of 86T1 (Seq. ID no. 1) is that of a 19 amino acid leader polypeptide, a 98 amino acid variable region, a 16 amino acid J region and a single globular constant region domain followed by transmembrane and cytoplasmic portions. By analogy to immunoglobulins, the two outermost cysteines in each globular domain would be linked and the last cysteine at position 260 would be bound to the other chain of the receptor heterodimer.

It was further found that antisera raised against synthetic peptide fragments of 86T1 (Seq. ID no. 1) can significantly inhibit the antigen-dependent release of IL-2 by T-helper hybridomas. It is therefore concluded that the locus described above represents a type of immunoglobulin gene specifically rearranged and expressed in at least some subsets of T-lymphocytes and that it plays a role in the recognition of antigen by T-cells.

The isolation and characterization of the $T_H$-Ag receptor α-unit will now be described. Procedures which have been described previously in isolating and characterizing the δ-subunit will not be repeated.

Calf thymus DNA was used to synthesize random prime $^{32}$P-labeled cDNA by standard procedures (Maniatis et al., supra) from polyA$^+$ cytoplasmic 2B4 mRNA. The cDNA was initially 700 nt average length and was allowed to fragment by autoradiolysis to about 300–400 nt in length over a two week period. Subtractive hybridization was then carried out employing hybridization and hydroxyapatite selection with $T_H$ hybridoma C10 mRNA, followed by the mRNA from the $T_H$-like lymphoma cell line EL-4. The twice subtracted probe was then hybridized to a filter of 2B4 cDNA library in the vector λ gt10. Approximately 20,000 plaques were screened. Seven positives were picked and rescreened with a probe of oligo-dT-primed cDNA made of membrane bound polysomal mRNA from 2B4, subtracted with mRNA from the P388D1 macrophage line (MBT*$_H$-Mac) Three of the seven positives were positive with the MBT*$_H$-Mac probe and two of these three cross-hybridized with each other. One of the cross-hybridizing probes was designated TT11 (Seq. ID no. 9) and chosen for further study. The TT11 (Seq. ID no. 9) cDNA clone was labeled by nick-translation and hybridized to a Northern blot containing a panel of mRNAs as follows: a) Bal17, B-cell lymphoma; b) M104e plasmacytoma; c) 3T3, fibroblast line; d) P338D1, macrophage line; e) 2B4; f) EL-4; g) BW5147. All are polyA$^+$ cytoplasmic RNAs prepared by standard procedures. A single band was observed at about 1.8 kb for 2B4, while two bands were observed for EL-4, a weaker band at 1.8 kb and a second band at 1.3 kb in the EL-4 lane.

To demonstrate that the gene encoding for the sequence of TT11 (Seq. ID no. 9) was as a result of a rearrangement, genomic DNAs from the livers of different mouse strains, various T-cell lines and hybrids of the B-cell lymphoma L10A were digested with a) HindIII; b) EcoRV; c) XbaI; d) BglII and electrophoresed through 0.7% agarose, blotted on nitrocellulose and hybridized by standard methods to a probe from the 5' half of TT11 (Seq. ID no. 9) (EcoRI-EcoRV, FIG. 3A). Two of the lanes designated FN1 and FN13 were from KLH reactive T H hybridomas derived from BALB/c×C57B/6 strain mice and the AKR strain thymoma line BW5147. A new band appears in a HindIII digest of FN1 with respect to parental DNAs, while one band in an EcoRV digest of AKR liver DNA disappears in BW5147 and an EcoRI digest shows a new band appearing in BW5147 versus the parental liver DNA. Two bands are observed which are polymorphic for an XbaI digest of C57B/6 DNA. Both of these bands are present in the FN1 hybrid, but only one occurs in FN13, which could only be the result of a rearrangement or partial deletion of the chromosome. A new band in FN1 versus the parentals is observed in a BglII digest. Although no one digest shows evidence of rearrangement in all T-cell DNAs, there are enough indications of such events to believe that TT11 is a T-cell receptor-like gene.

The TT11 cDNA clone was partially sequenced by the procedure of Maxam and Gilbert, Meth. Enzym. (1980) 65:499–560, utilizing the strategies shown in FIG. 3A and the sequences shown in FIG. 3B (Seq. ID no. 9). The clone was oriented by a polyA stretch (about 150 nt) at the 3'-end and sequencing of the 5' half revealed a long open reading frame of 810 nt, with an initiation codon (ATG) within the first 12 nt. This sequence has regions similar to the Ig leader, variable region, joining (J) region, and constant region, just as do the T-cell receptor β-chain and the HDS4 gene clone of Saito et al., Nature (1984) 309:757–762.

Features of the sequence are an extra cysteine outside of the putative intra-domain cysteines in the constant region (common to the latter two T-cell specific genes), followed by a transmembrane region and a cytoplasmic region, all of which are encoded as separate exons in the β-chain genes. There are four potential N-linked glycosylation sites, similar to the four or five found in different β-chain sequences. It would appear that only three of these four potential sites are available for glycosylation since the most carboxy terminal one is embedded in the transmembrane region.

The exact position of processing of the T-cell receptor α-subunit has not been established, but by analogy to immunoglobulin types, it would be just before the glutamine at +1 shown in FIG. 3B. Alternatively, based on the N-terminal amino acid sequence of the human β-chain from the REX T-cell line (Acuto et al., Proc. Natl. Acad. Sci. USA (1984) 81:3851–3855) the processing point would be just before the asparagine at +3. In the first place, the molecular weight would be 27 kd, which agrees with the molecular weight observed by Allison et al., who obtained a molecular weight of 27 kd from a murine α-chain stripped of N-linked sugars with endo F.

The overall homology with the V and C regions of Ig counterparts is relatively low (10–26%). However, many of the conserved residues found in all the five known Ig-like genes are present, particularly in the V region and the J region elements. The spacing of the cysteines in the TT11 (Seq. ID no. 9) variable region is 65 amino acids, which is identical to that of the light chains, and the sequence "WYRQ" (Seq. ID no. 11) starting at residue 35 and "DSA-Y-CAV" (Seq. ID no. 12) at residues 83–91 are also highly conserved in most I-, G- and T-cell receptor V regions. As with the α-chain and HDS4, the J region in the most highly conserved portion, with 7/16 residues homologous to the β-chain consensus sequence (Gascoigne et al., Nature (1984) 310:387–891) and 9/16 the same as J T 3, (Gascoigne et al., supra). TT11 (Seq. ID no. 9) has the sequence "ILLLK" (Seq. ID no. 13) in the transmembrane region, characteristic of T-cell receptor sequences, where the conservation of a charged amino acid (lysine or arginine) in a transmembrane is unusual and not found in other members of the immunoglobulin super family.

While not established, there appears to be strong support that there is a D region present in the α-subunit. In particular, just 5' to the "SGN" amino acid sequence of the J region (which marks the 5' border of J T 3 in the beta gene complex), there is a nucleotide sequence "GGGGG". This is characteristic of gene D regions of the β-subunit, where 7 out of 14 contain runs of between 3–7 Gs on their 3' side (Tonegawa, Nature (1983) 302:575–581). The Northern blot data described previously further support the presence of a D region. The two bands clearly visible in the EL-4 lane, and observed in other T H lines, is characteristic of the DJC transcript of the β-chain which is 300 nt shorter than the VDJC transcript (Kavaler et al., Nature (1984) 310:421–423).

To establish the ratio of the mRNAs for the α- and β-subunits, thymocyte, conA (concanavalin A) stimulated spleen and 2B4 cDNA libraries were surveyed with TT11, HDS4 and $C_T\beta$ beta probes. Whereas TT11 and $C_T\beta$ are present in fairly similar frequencies, 1:1–1:3 in the 2B4 and conA spleen libraries, respectively, HDS4 is much rarer. A substantial change in ratio of TT11 to β-chain in immature versus mature T-cells was observed suggesting that TT11 gene expression may come after expression of β-chain, analogous to light chain immunoglobulin expression following that of the heavy chain in B-cells.

It is evident from the above results that novel DNA sequences and constructs are provided which provide for the expression of T-cell antigen receptors, subunits and fragments thereof. The DNA sequences can be used in a variety of ways to produce hybrid proteins, which may be retained as surface membrane proteins, can be labeled to provide for probes for determining lymphocyte origin or type, for isolating DNA sequences from T-cells, for use as primers for producing DNA sequences coding for the T-cell receptor subunits, or for use for secretion of foreign proteins from a mammalian host cell. The peptides can be used for the production of antibodies for isolation of T-cell antigen receptors, for removal of T-cells from cell-mixtures, for identification of T-cells, or for binding to T-cells in vivo or in vitro, so as to affect their viability, proliferation, secretion of factors, or the like.

Although the foregoing invention has been described in some detail by way of illustration and example for purposes of clarity of understanding, it will be obvious that certain changes and modifications may be practiced within the scope of the appended claims.

BIOLOGICAL DEPOSIT

TM86 (Seq. ID no. 7) was deposited at the A.T.C.C. on Mar. 1, 1984 and given Accession No. 40099. TT11 (Seq. ID no. 9) was deposited at the A.T.C.C. on Oct. 22, 1984 and given Accession No. 40141.

What is claimed is:

1. A T cell receptor β subunit peptide or polypeptide, said peptide or polypeptide either chemically-synthesized, recombinantly-expressed, or combined with a heterologous amino acid sequence in a protein hybrid, wherein said peptide or polypeptide is detectably labeled.

2. The peptide or polypeptide of claim 1, wherein said label is a radionuclide.

3. The peptide or polypeptide of claim 1, wherein said label is an NMR active compound.

4. The peptide or polypeptide of claim 1, wherein said label is a fluorescer.

5. A T cell receptor β subunit peptide or polypeptide, wherein said peptide or polypeptide is either chemically-synthesized, recombinantly-expressed, or combined with a heterologous amino acid sequence in a protein hybrid, wherein said peptide or polypeptide is conjugated to a toxin.

6. A pharmaceutical composition comprising the peptide or polypeptide of claims 1 or 5 and a pharmaceutically acceptable carrier.

* * * * *

SEQUENCE LISTING

```
<160> NUMBER OF SEQ ID NOS: 15

<210> SEQ ID NO 1
<211> LENGTH: 940
<212> TYPE: DNA
<213> ORGANISM: Mus musculus
<220> FEATURE:
<221> NAME/KEY: CDS
```

-continued

```
<222> LOCATION: (23)..(940)
<220> FEATURE:
<223> OTHER INFORMATION: "n" at position 940 may be an A, T, C or G
      (i.e., a wobble position that was not in fact sequenced,
      although those skilled in the art would understand that an A, T, C
      or G at that position would result in the translation of a
      Serine); "n" was introduced at position 940, therefore, solely as
      a place keeper in order to conceptually translate the
      nucleotide sequence.

<400> SEQUENCE: 1
ccgtctggag cctgattcca cc atg agc tgc agg ctt ctc ctc tat gtt tcc        52
                         Met Ser Cys Arg Leu Leu Leu Tyr Val Ser
                          1               5                  10 cta tgt ctt gtg gaa aca gca ctc atg aac act aaa att act cag tca       100
Leu Cys Leu Val Glu Thr Ala Leu Met Asn Thr Lys Ile Thr Gln Ser
             15                  20                  25 cca aga tat cta atc ttg gga aga gca aat aag tct ttg gaa tgt gag       148
Pro Arg Tyr Leu Ile Leu Gly Arg Ala Asn Lys Ser Leu Glu Cys Glu
         30                  35                  40 caa cat ctg gga cat aat gct atg tac tgg tat aaa cag agc gct gag       196
Gln His Leu Gly His Asn Ala Met Tyr Trp Tyr Lys Gln Ser Ala Glu
     45                  50                  55 aag ccg cca gag ctc atg ttt ctc tac aat ctt aaa cag ttg att cga       244
Lys Pro Pro Glu Leu Met Phe Leu Tyr Asn Leu Lys Gln Leu Ile Arg
 60                  65                  70 aat gag acg gtg ccc agt cgt ttt ata cct gaa tgc cca gac agc tcc       292
Asn Glu Thr Val Pro Ser Arg Phe Ile Pro Glu Cys Pro Asp Ser Ser
 75                  80                  85                  90 aag cta ctt tta cat ata tct gcc gtg gat cca gaa gac tca gct gtc       340
Lys Leu Leu Leu His Ile Ser Ala Val Asp Pro Glu Asp Ser Ala Val
                 95                 100                 105 tat ttt tgt gcc agc agc cac gga cag ggg gtt tct gga aat acg ctc       388
Tyr Phe Cys Ala Ser Ser His Gly Gln Gly Val Ser Gly Asn Thr Leu
             110                 115                 120 tat ttt gga gaa gga agc cgg ctc att gtt gta gag gat ctg aga aat       436
Tyr Phe Gly Glu Gly Ser Arg Leu Ile Val Val Glu Asp Leu Arg Asn
         125                 130                 135 gtg act cca ccc aag gtc tcc ttg ttt gag cca tca aaa gca gag att       484
Val Thr Pro Pro Lys Val Ser Leu Phe Glu Pro Ser Lys Ala Glu Ile
     140                 145                 150 gca aac aaa caa aag gct acc ctc gtg tgc ttg gcc agg ggc ttc ttc       532
Ala Asn Lys Gln Lys Ala Thr Leu Val Cys Leu Ala Arg Gly Phe Phe
155                 160                 165                 170 cct gac cac gtg gag ctg agc tgg tgg gtg aat ggc aag gag gtc cac       580
Pro Asp His Val Glu Leu Ser Trp Trp Val Asn Gly Lys Glu Val His
                 175                 180                 185 agt ggg gtc agc acg gac cct cag gcc tac aag gag agc aat tat agc       628
Ser Gly Val Ser Thr Asp Pro Gln Ala Tyr Lys Glu Ser Asn Tyr Ser
             190                 195                 200 cac tgc ctg agc agc cgc ctg agg gtc tct gct acc ttc tgg cac aat       676
His Cys Leu Ser Ser Arg Leu Arg Val Ser Ala Thr Phe Trp His Asn
         205                 210                 215 cct cgc aac cac ttc cgc tgc caa gtg cag ttc cat ggg ctt tca gag       724
Pro Arg Asn His Phe Arg Cys Gln Val Gln Phe His Gly Leu Ser Glu
     220                 225                 230 gag gac aag tgg cca gag ggc tca ccc aaa cct gtc aca cag aac atc       772
Glu Asp Lys Trp Pro Glu Gly Ser Pro Lys Pro Val Thr Gln Asn Ile
235                 240                 245                 250 agt gca gag gcc tgg ggc cga gca gac tgt ggg att acc tca gca tcc       820
Ser Ala Glu Ala Trp Gly Arg Ala Asp Cys Gly Ile Thr Ser Ala Ser
                 255                 260                 265
```

```
tat caa caa ggg gtc ttg tct gcc acc atc ctc tat gag atc ctg cta    868
Tyr Gln Gln Gly Val Leu Ser Ala Thr Ile Leu Tyr Glu Ile Leu Leu
            270                 275                 280 ggg aaa gcc acc ctg tat gct gtg ctt gtc agt aca ctg gtg gtg atg    916
Gly Lys Ala Thr Leu Tyr Ala Val Leu Val Ser Thr Leu Val Val Met
        285                 290                 295 gct atg gtc aaa aga aag aat tcn                                    940
Ala Met Val Lys Arg Lys Asn Ser
    300                 305
```

<210> SEQ ID NO 2
<211> LENGTH: 306
<212> TYPE: PRT
<213> ORGANISM: Mus musculus

<400> SEQUENCE: 2

```
Met Ser Cys Arg Leu Leu Leu Tyr Val Ser Leu Cys Leu Val Glu Thr
 1               5                  10                  15

Ala Leu Met Asn Thr Lys Ile Thr Gln Ser Pro Arg Tyr Leu Ile Leu
            20                  25                  30

Gly Arg Ala Asn Lys Ser Leu Glu Cys Glu Gln His Leu Gly His Asn
        35                  40                  45

Ala Met Tyr Trp Tyr Lys Gln Ser Ala Glu Lys Pro Pro Glu Leu Met
    50                  55                  60

Phe Leu Tyr Asn Leu Lys Gln Leu Ile Arg Asn Glu Thr Val Pro Ser
 65                  70                  75                  80

Arg Phe Ile Pro Glu Cys Pro Asp Ser Ser Lys Leu Leu Leu His Ile
                85                  90                  95

Ser Ala Val Asp Pro Glu Asp Ser Ala Val Tyr Phe Cys Ala Ser Ser
            100                 105                 110

His Gly Gln Gly Val Ser Gly Asn Thr Leu Tyr Phe Gly Glu Gly Ser
        115                 120                 125

Arg Leu Ile Val Val Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser His Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300
```

Asn Ser
305

<210> SEQ ID NO 3
<211> LENGTH: 389
<212> TYPE: DNA
<213> ORGANISM: Mus musculus
<220> FEATURE:
<221> NAME/KEY: CDS
<222> LOCATION: (3..17, 24..134, 138..149, 153..302, 306..389)

<400> SEQUENCE: 3

```
ag gtt tac att tct gtt taatag ttc atc aag agt tta gtg cct tta        47
   Val Tyr Ile Ser Val        Phe Ile Lys Ser Leu Val Pro Leu
    1           5                      10 ttg cct cta caa gct ggt tac aaa tta att tta att aac tcc cac tta       95
Leu Pro Leu Gln Ala Gly Tyr Lys Leu Ile Leu Ile Asn Ser His Leu
     15              20                  25 tta aaa aaa tct gca gtt ctt tgt gag aca cgt att cat taa aaa aaa     143
Leu Lys Lys Ser Ala Val Leu Cys Glu Thr Arg Ile His     Lys Lys
         30              35              40 tca aca taa gta aaa ggc aaa att aaa aca cac cac acc aaa aat aag     191
Ser Thr     Val Lys Gly Lys Ile Lys Thr His His Thr Lys Asn Lys
 45              50                  55 cac tgt aaa ttt ttt gat acg tat aat tat aca tgt aca cac ata att     239
His Cys Lys Phe Phe Asp Thr Tyr Asn Tyr Thr Cys Thr His Ile Ile
 60              65                  70                  75 agg aat ttt cct atc tat gtg acc att ttc agc cct ttc tta caa gat     287
Arg Asn Phe Pro Ile Tyr Val Thr Ile Phe Ser Pro Phe Leu Gln Asp
                 80                  85                  90 caa ggc aga tcc aga tag ctc tca gac cat tcg tac tct ctt tac ttt     335
Gln Gly Arg Ser Arg     Leu Ser Asp His Ser Tyr Ser Leu Tyr Phe
             95                 100                 105 cca gag gat ctg aga aat gtg act cca ccc aag gtc tcc ttg ttt gag     383
Pro Glu Asp Leu Arg Asn Val Thr Pro Pro Lys Val Ser Leu Phe Glu
         110                 115                 120 cca tca                                                              389
Pro Ser
```

<210> SEQ ID NO 4
<211> LENGTH: 124
<212> TYPE: PRT
<213> ORGANISM: Mus musculus

<400> SEQUENCE: 4

Val Tyr Ile Ser Val Phe Ile Lys Ser Leu Val Pro Leu Pro Leu
 1               5                  10                  15

Gln Ala Gly Tyr Lys Leu Ile Leu Ile Asn Ser His Leu Leu Lys Lys
             20                  25                  30

Ser Ala Val Leu Cys Glu Thr Arg Ile His Lys Lys Ser Thr Val Lys
         35                  40                  45

Gly Lys Ile Lys Thr His His Thr Lys Asn Lys His Cys Lys Phe Phe
     50                  55                  60

Asp Thr Tyr Asn Tyr Thr Cys Thr His Ile Ile Arg Asn Phe Pro Ile
 65                  70                  75                  80

Tyr Val Thr Ile Phe Ser Pro Phe Leu Gln Asp Gln Gly Arg Ser Arg
                 85                  90                  95

Leu Ser Asp His Ser Tyr Ser Leu Tyr Phe Pro Glu Asp Leu Arg Asn
             100                 105                 110

Val Thr Pro Pro Lys Val Ser Leu Phe Glu Pro Ser

```
            115                 120

<210> SEQ ID NO 5
<211> LENGTH: 198
<212> TYPE: DNA
<213> ORGANISM: Mus musculus
<220> FEATURE:
<221> NAME/KEY: CDS
<222> LOCATION: (1)..(198)

<400> SEQUENCE: 5 aga gga gca gct tat ctg gtg gtt tct tcc agc cct caa ggg gta gac     48
Arg Gly Ala Ala Tyr Leu Val Val Ser Ser Pro Gln Gly Val Asp
 1               5                  10                  15 cta tgg gag ggt ccc ttt ttg tat aaa gct gta aca ttg tgg gga cag     96
Leu Trp Glu Gly Pro Phe Leu Tyr Lys Ala Val Thr Leu Trp Gly Gln
                20                  25                  30 gat tct gga aat acg ctc tat ttt gga gaa gga agc cgg ctc att gtt    144
Asp Ser Gly Asn Thr Leu Tyr Phe Gly Glu Gly Ser Arg Leu Ile Val
            35                  40                  45 gta gag gat ctg aga aat gtg act cca ccc aag gtc tcc ttg ttt gag    192
Val Glu Asp Leu Arg Asn Val Thr Pro Pro Lys Val Ser Leu Phe Glu
        50                  55                  60 cca tca                                                            198
Pro Ser
 65

<210> SEQ ID NO 6
<211> LENGTH: 66
<212> TYPE: PRT
<213> ORGANISM: Mus musculus

<400> SEQUENCE: 6

Arg Gly Ala Ala Tyr Leu Val Val Ser Ser Pro Gln Gly Val Asp
 1               5                  10                  15

Leu Trp Glu Gly Pro Phe Leu Tyr Lys Ala Val Thr Leu Trp Gly Gln
                20                  25                  30

Asp Ser Gly Asn Thr Leu Tyr Phe Gly Glu Gly Ser Arg Leu Ile Val
            35                  40                  45

Val Glu Asp Leu Arg Asn Val Thr Pro Pro Lys Val Ser Leu Phe Glu
        50                  55                  60

Pro Ser
 65

<210> SEQ ID NO 7
<211> LENGTH: 157
<212> TYPE: DNA
<213> ORGANISM: Mus musculus
<220> FEATURE:
<221> NAME/KEY: CDS
<222> LOCATION: (2)..(157)

<400> SEQUENCE: 7 a ggc acc tgt ggg gaa gaa act ttt ttg tat cac gat gta aca ttg tgg   49
  Gly Thr Cys Gly Glu Glu Thr Phe Leu Tyr His Asp Val Thr Leu Trp
   1               5                  10                  15 gga ctg ggg gcc caa gac acc cag tac ttt ggg cca ggc act cgg ctc    97
Gly Leu Gly Ala Gln Asp Thr Gln Tyr Phe Gly Pro Gly Thr Arg Leu
                20                  25                  30 ctc gtg tta gag gat ctg aga aat gtg act cca ccc aag gtc tcc ttg   145
Leu Val Leu Glu Asp Leu Arg Asn Val Thr Pro Pro Lys Val Ser Leu
            35                  40                  45
```

```
ttt cag cca tca                                                          157
Phe Gln Pro Ser
     50

<210> SEQ ID NO 8
<211> LENGTH: 52
<212> TYPE: PRT
<213> ORGANISM: Mus musculus

<400> SEQUENCE: 8

Gly Thr Cys Gly Glu Glu Thr Phe Leu Tyr His Asp Val Thr Leu Trp
 1               5                  10                  15

Gly Leu Gly Ala Gln Asp Thr Gln Tyr Phe Gly Pro Gly Thr Arg Leu
             20                  25                  30

Leu Val Leu Glu Asp Leu Arg Asn Val Thr Pro Pro Lys Val Ser Leu
         35                  40                  45

Phe Gln Pro Ser
     50

<210> SEQ ID NO 9
<211> LENGTH: 990
<212> TYPE: DNA
<213> ORGANISM: Mus musculus
<220> FEATURE:
<221> NAME/KEY: CDS
<222> LOCATION: (12)..(821)
<220> FEATURE:
<221> NAME/KEY: Signal peptide
<222> LOCATION: (12)..(71)
<220> FEATURE:
<221> NAME/KEY: Mature peptide
<222> LOCATION: (72)..(821)

<400> SEQUENCE: 9
aggaggagag a atg aac tcc ttg agt gtt tcc cta gtg gtc ctg tgg ctc    50
           Met Asn Ser Leu Ser Val Ser Leu Val Val Leu Trp Leu
              -20                 -15                 -10 ctg tta aac tgg gtg aac agc cag cag aat gtg cag cag agc cca gaa    98
Leu Leu Asn Trp Val Asn Ser Gln Gln Asn Val Gln Gln Ser Pro Glu
         -5                   1                   5 tcc ctc att gtc cca gag gga gcc agg acc tct ctc aac tgc act ttc   146
Ser Leu Ile Val Pro Glu Gly Ala Arg Thr Ser Leu Asn Cys Thr Phe
 10                  15                  20                  25 agt gac agt gct tct cag tat ttc tgg tgg tac aga cag cat tct ggg   194
Ser Asp Ser Ala Ser Gln Tyr Phe Trp Trp Tyr Arg Gln His Ser Gly
                 30                  35                  40 aaa gcc ccc aag gca ctg atg tcc atc ttc tcc aat ggt gaa aaa gaa   242
Lys Ala Pro Lys Ala Leu Met Ser Ile Phe Ser Asn Gly Glu Lys Glu
             45                  50                  55 gaa ggg aga ttc aca att cac ctc aat aaa gcc agt ctg cat ttc tcc   290
Glu Gly Arg Phe Thr Ile His Leu Asn Lys Ala Ser Leu His Phe Ser
         60                  65                  70 ctg cac atc aga gac tcc cag ccc agt gac tct gct ctc tat ctc tgt   338
Leu His Ile Arg Asp Ser Gln Pro Ser Asp Ser Ala Leu Tyr Leu Cys
     75                  80                  85 gca gtg acc ctt tat ggg ggc agt ggc aac aag ctc atc ttt gga act   386
Ala Val Thr Leu Tyr Gly Gly Ser Gly Asn Lys Leu Ile Phe Gly Thr
 90                  95                 100                 105 ggc act ctg ctt tct gtc aag cca aac atc cag aac cca gaa cct gct   434
Gly Thr Leu Leu Ser Val Lys Pro Asn Ile Gln Asn Pro Glu Pro Ala
                110                 115                 120 gtg tac cag tta aaa gat cct cgg tct cag gac agc acc ctc tgc ctg   482
Val Tyr Gln Leu Lys Asp Pro Arg Ser Gln Asp Ser Thr Leu Cys Leu
```

-continued

```
                    125                      130                      135
ttc acc gac ttt gac tcc caa atc aat gtg ccg aaa acc atg gaa tct        530
Phe Thr Asp Phe Asp Ser Gln Ile Asn Val Pro Lys Thr Met Glu Ser
            140                      145                      150 gga acg ttc atc act gac aaa act gtg ctg gac atg aaa gct atg gat        578
Gly Thr Phe Ile Thr Asp Lys Thr Val Leu Asp Met Lys Ala Met Asp
        155                      160                      165 tcc aag agc aat ggg gcc att gcc tgg agc aac cag aca agc ttc acc        626
Ser Lys Ser Asn Gly Ala Ile Ala Trp Ser Asn Gln Thr Ser Phe Thr
170                      175                      180                      185 tgc caa gat atc ttc aaa gag acc aac gcc acc tac ccc agt tca gac        674
Cys Gln Asp Ile Phe Lys Glu Thr Asn Ala Thr Tyr Pro Ser Ser Asp
                    190                      195                      200 gtt ccc tgt gat gcc acg ttg acc gag aaa agc ttt gaa aca gat atg        722
Val Pro Cys Asp Ala Thr Leu Thr Glu Lys Ser Phe Glu Thr Asp Met
                205                      210                      215 aac cta aac ttt caa aac ctg tca gtt atg gga ctc cga atc ctc ctg        770
Asn Leu Asn Phe Gln Asn Leu Ser Val Met Gly Leu Arg Ile Leu Leu
            220                      225                      230 ctg aaa gta gcg gga ttt aac ctg ctc atg acg ctg agg ctg tgg tcc        818
Leu Lys Val Ala Gly Phe Asn Leu Leu Met Thr Leu Arg Leu Trp Ser
        235                      240                      245 agt tga ggtctgcaag actgacagag cctgactccc aagttccgtc ctcctcaccc        874
Ser
250 ctccgctccc tcttcaagcc aaaggagcc ggctgtctgg ggtctggttg gccctgattc        934 acaatcccac ctagatctcc cagatttgtg aggaaggttg ctagagagct aagcgc          990
```

<210> SEQ ID NO 10
<211> LENGTH: 270
<212> TYPE: PRT
<213> ORGANISM: Mus musculus

<400> SEQUENCE: 10

```
Met Asn Ser Leu Ser Val Ser Leu Val Val Leu Trp Leu Leu Leu Asn
-20              -15                  -10                   -5

Trp Val Asn Ser Gln Gln Asn Val Gln Gln Ser Pro Glu Ser Leu Ile
             1                   5                  10

Val Pro Glu Gly Ala Arg Thr Ser Leu Asn Cys Thr Phe Ser Asp Ser
            15                  20                  25

Ala Ser Gln Tyr Phe Trp Trp Tyr Arg Gln His Ser Gly Lys Ala Pro
        30                  35                      40

Lys Ala Leu Met Ser Ile Phe Ser Asn Gly Glu Lys Glu Glu Gly Arg
45                  50                  55                      60

Phe Thr Ile His Leu Asn Lys Ala Ser Leu His Phe Ser Leu His Ile
                65                  70                      75

Arg Asp Ser Gln Pro Ser Asp Ser Ala Leu Tyr Leu Cys Ala Val Thr
            80                  85                      90

Leu Tyr Gly Gly Ser Gly Asn Lys Leu Ile Phe Gly Thr Gly Thr Leu
        95                  100                     105

Leu Ser Val Lys Pro Asn Ile Gln Asn Pro Glu Pro Ala Val Tyr Gln
    110                     115                     120

Leu Lys Asp Pro Arg Ser Gln Asp Ser Thr Leu Cys Leu Phe Thr Asp
125                     130                     135                 140

Phe Asp Ser Gln Ile Asn Val Pro Lys Thr Met Glu Ser Gly Thr Phe
                145                     150                     155
```

-continued

```
Ile Thr Asp Lys Thr Val Leu Asp Met Lys Ala Met Asp Ser Lys Ser
            160                 165                 170

Asn Gly Ala Ile Ala Trp Ser Asn Gln Thr Ser Phe Thr Cys Gln Asp
        175                 180                 185

Ile Phe Lys Glu Thr Asn Ala Thr Tyr Pro Ser Ser Asp Val Pro Cys
    190                 195                 200

Asp Ala Thr Leu Thr Glu Lys Ser Phe Glu Thr Asp Met Asn Leu Asn
205                 210                 215                 220

Phe Gln Asn Leu Ser Val Met Gly Leu Arg Ile Leu Leu Leu Lys Val
                225                 230                 235

Ala Gly Phe Asn Leu Leu Met Thr Leu Arg Leu Trp Ser Ser
                240                 245                 250

<210> SEQ ID NO 11
<211> LENGTH: 4
<212> TYPE: PRT
<213> ORGANISM: Mus musculus

<400> SEQUENCE: 11

Trp Tyr Arg Gln
  1

<210> SEQ ID NO 12
<211> LENGTH: 9
<212> TYPE: PRT
<213> ORGANISM: Mus musculus
<220> FEATURE:
<223> OTHER INFORMATION: Xaa at positions 4 & 6 may be any amino acid

<400> SEQUENCE: 12

Asp Ser Ala Xaa Tyr Xaa Cys Ala Val
  1               5

<210> SEQ ID NO 13
<211> LENGTH: 5
<212> TYPE: PRT
<213> ORGANISM: Mus musculus

<400> SEQUENCE: 13

Ile Leu Leu Leu Lys
  1               5

<210> SEQ ID NO 14
<211> LENGTH: 4
<212> TYPE: PRT
<213> ORGANISM: Mus musculus

<400> SEQUENCE: 14

Trp Tyr Lys Gln
  1

<210> SEQ ID NO 15
<211> LENGTH: 5
<212> TYPE: PRT
<213> ORGANISM: Mus musculus

<400> SEQUENCE: 15

Ile Leu Leu Gly Lys
  1               5
```